United States Patent
Ma et al.

(10) Patent No.: US 11,571,389 B2
(45) Date of Patent: Feb. 7, 2023

(54) DELIVERY DEVICES AND METHODS FOR MAKING THE SAME

(71) Applicant: THE REGENTS OF THE UNIVERSITY OF MICHIGAN, Ann Arbor, MI (US)

(72) Inventors: Peter X. Ma, Ann Arbor, MI (US); Ming Dang, Maple Grove, MN (US); Laurie K. McCauley, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 691 days.

(21) Appl. No.: 16/335,947

(22) PCT Filed: Sep. 21, 2017

(86) PCT No.: PCT/US2017/052670
§ 371 (c)(1),
(2) Date: Mar. 22, 2019

(87) PCT Pub. No.: WO2018/057709
PCT Pub. Date: Mar. 29, 2018

(65) Prior Publication Data
US 2019/0307697 A1    Oct. 10, 2019

Related U.S. Application Data

(60) Provisional application No. 62/399,126, filed on Sep. 23, 2016.

(51) Int. Cl.
*A61K 9/20* (2006.01)
*A61K 9/70* (2006.01)
(Continued)

(52) U.S. Cl.
CPC .......... *A61K 9/2031* (2013.01); *A61K 9/0024* (2013.01); *A61K 9/204* (2013.01);
(Continued)

(58) Field of Classification Search
CPC .. A61K 9/7007; A61K 9/2086; A61K 9/7092; B29C 41/006
See application file for complete search history.

(56) References Cited

U.S. PATENT DOCUMENTS

2004/0034357 A1* 2/2004 Beane ..................... A61L 31/16
606/232
2007/0249536 A1   10/2007 Ma et al.
(Continued)

FOREIGN PATENT DOCUMENTS

WO  WO 2005/102284   11/2005
WO  WO 2008/128140   10/2008

OTHER PUBLICATIONS

International Search Report and Written Opinion for International Application No. PCT/US2017/052670 dated Dec. 4, 2017, 10 pages.
(Continued)

*Primary Examiner* — Bhisma Mehta
*Assistant Examiner* — John J Crawford
(74) *Attorney, Agent, or Firm* — Dierker & Kavanaugh, P.C.

(57) ABSTRACT

In an example of a method for making a pulsatile delivery device, one type of charges are generated on a polymeric layer, and charges opposite the one type of charges are generated on a delivery layer including a film forming material and a predetermined substance dispersed throughout the film forming material. The charged polymeric and delivery layers are placed into contact to form a bi-layer structure. A stack with at least two bi-layer structures is
(Continued)

formed so that the polymeric layers and the delivery layers are alternating throughout the stack. The stack is sealed so that one of the polymeric layers remains exposed.

12 Claims, 31 Drawing Sheets

(51) Int. Cl.
    *A61K 38/29*     (2006.01)
    *A61K 9/00*     (2006.01)
    *A61K 9/50*     (2006.01)
    *A61K 47/34*     (2017.01)

(52) U.S. Cl.
    CPC ............ *A61K 9/205* (2013.01); *A61K 9/7007* (2013.01); *A61K 38/29* (2013.01); *A61K 47/34* (2013.01); *A61K 9/5031* (2013.01)

(56) References Cited

U.S. PATENT DOCUMENTS

| | | | | |
|---|---|---|---|---|
| 2008/0254095 | A1* | 10/2008 | Ma | A61K 38/29 514/1.1 |
| 2009/0258045 | A1* | 10/2009 | Chuang | A61L 27/54 424/409 |
| 2010/0040674 | A1* | 2/2010 | Smith | A61L 27/58 424/443 |
| 2013/0164347 | A1 | 6/2013 | Gensini et al. | |
| 2014/0093575 | A1* | 4/2014 | Hammond | A61K 9/5161 424/491 |

OTHER PUBLICATIONS

Liu et al., "Pulsatile Release of Parathyroid Hormone from an Implantable Delivery System", Biomaterials Oct. 2007; 28(28): 4124-4131, 18 pages.

* cited by examiner

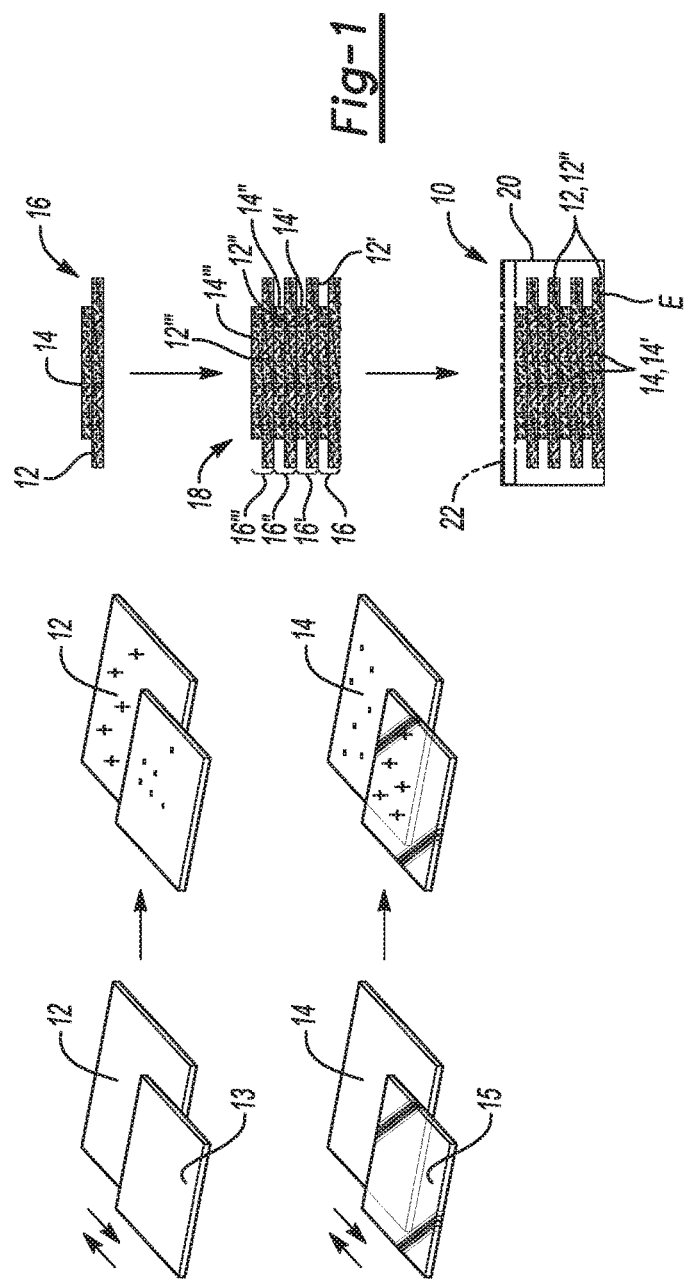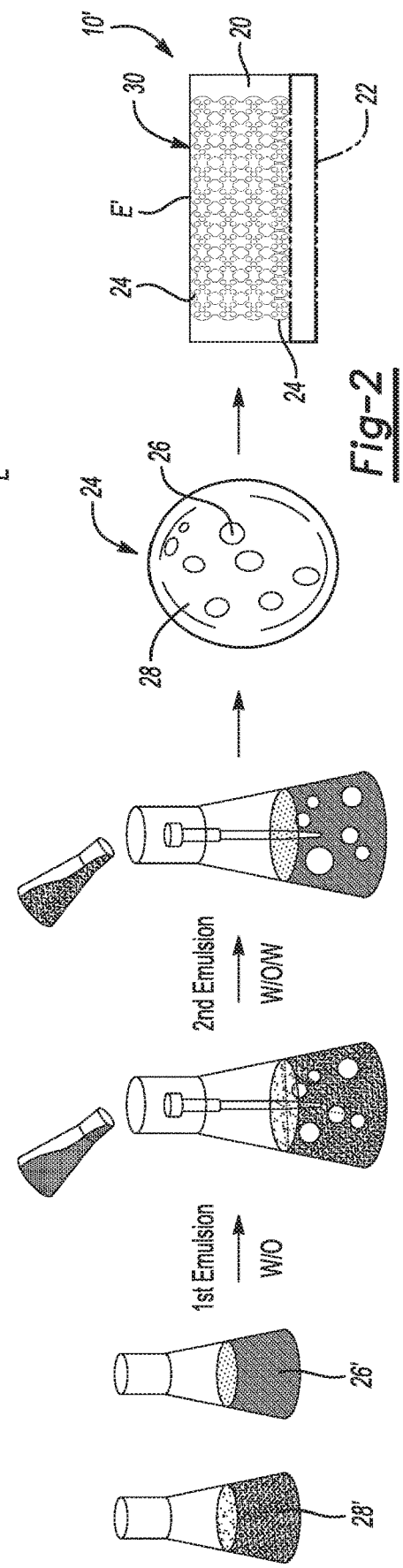
Fig-1
Fig-2

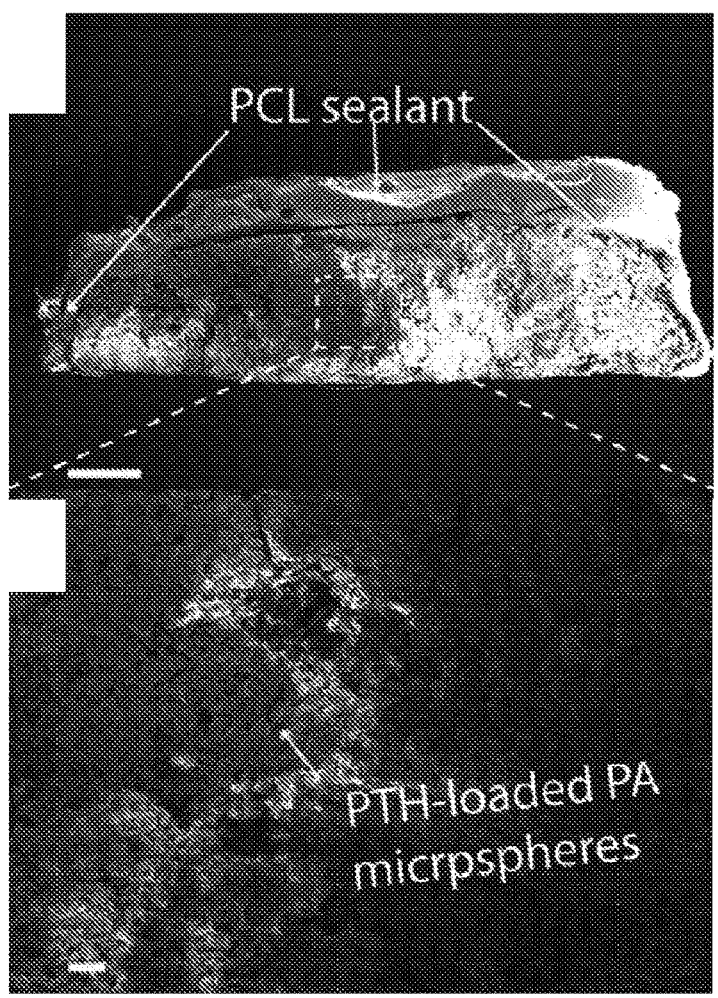
*Fig-27A*
*Fig-27B*
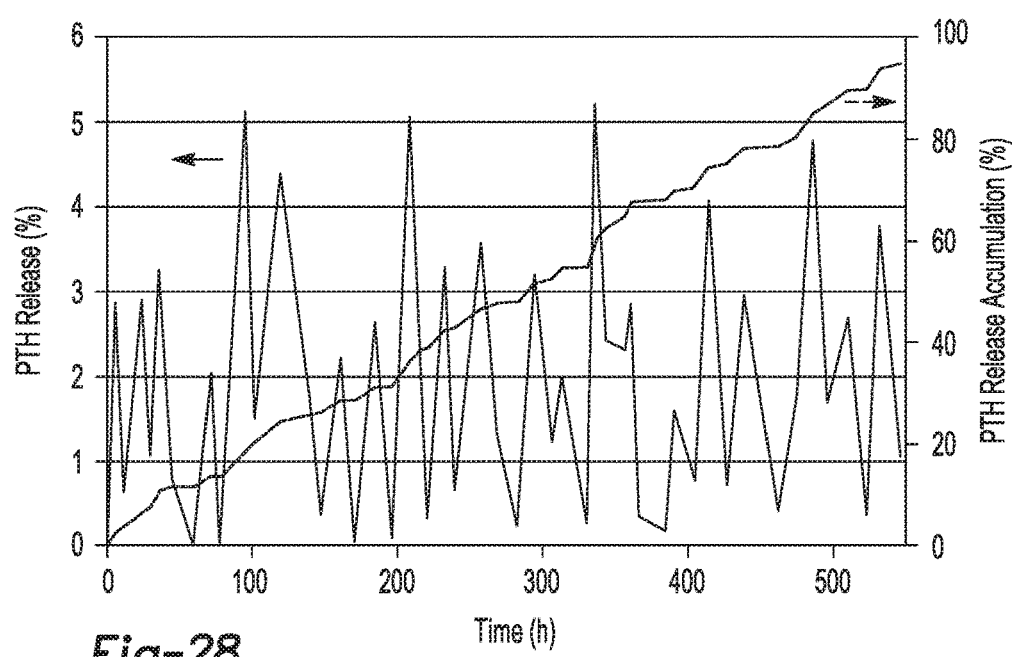
*Fig-28*

DELIVERY DEVICES AND METHODS FOR MAKING THE SAME

CROSS-REFERENCE TO RELATED APPLICATIONS

This application claims the benefit of U.S. provisional application Ser. No. 62/399,126, filed Sep. 23, 2016, the contents of which is incorporated by reference herein in its entirety.

STATEMENT REGARDING FEDERALLY SPONSORED RESEARCH OR DEVELOPMENT

This invention was made with government support under Grant No. W81XWH-12-2-0008 awarded by the U.S. Army Medical Research and Material Command, and under Grant Nos. DE022327 and DK053904 awarded by the National Institutes of Health (NIH). The government has certain rights in the invention.

BACKGROUND

Biological systems are sensitive to the location and timing of physiological signals and therapeutics. For example, to eliminate pain or to correct an endocrine disorder, a suitable drug should be delivered at specific time points and follow a certain pattern. Controlled release systems have been developed to achieve prolonged and sustained delivery of biological compound(s). However, there has been limited progress in controlled release systems to harness the spatiotemporal sensitivity of a patient to a biological compound in order to enable or optimize its therapeutic effect.

Different biological compounds may have different effects, depending on the dosage and delivery pattern or mode of administration. For example, the anabolic or catabolic action of parathyroid hormone (PTH) depends on the pattern of delivery. Generally, continuous delivery of PTH leads to catabolic effects (e.g., bone resorption), while pulsatile (intermittent) delivery of PTH results in anabolic effects on bone (e.g., improves bone micro-architecture, mineral density, and strength).

To achieve pulsatile delivery of a biological compound (e.g., of PTH), a variety of different platforms (e.g., micelles, liposomes, micro/nanoparticles, hydrogels, and microchips) have been used in controlled release systems. Based on the triggering mechanisms, these delivery systems can be classified as stimuli-responsive pulsatile release systems and self-regulated pulsatile release systems. In stimuli-responsive systems, carriers release the loaded biological compound when triggered by external stimuli, such as temperature, pH, light, enzyme, ultrasound, and electric or magnetic fields. These responsive systems can achieve pulsatile release, but are limited in that they have an initial burst release, an irreversible triggered release, a short time interval (seconds to minutes) release, or a short release duration. Moreover, the stimuli may not be suitable or desirable for patient use. In self-regulated release systems, the biological compounds are loaded in reservoirs sealed by a barrier material, which is usually composed of an erodible or biodegradable polymer. After the barrier material is eroded or degraded, the compounds are rapidly released from the inner reservoir. These systems are usually biocompatible and biodegradable, but multiple barriers or coatings may be required to achieve the desired multiple pulses of release. Multiple layers may, however, pose challenges with material properties and device fabrication technologies, often resulting in inconsistency.

BRIEF DESCRIPTION OF THE DRAWINGS

Features of examples of the present disclosure will become apparent by reference to the following detailed description and drawings, in which like reference numerals correspond to the same or similar, though perhaps not identical, components. For the sake of brevity, reference numerals having a previously described function may or may not be described in connection with subsequent drawings in which they appear.

FIG. 1 is a schematic flow diagram illustrating an example of a method for forming an example of a pulsatile delivery device;

FIG. 2 is a schematic flow diagram illustrating an example of a method for forming an example of a continuous delivery device;

FIGS. 27A and 27B are SEM images of a PTH continuous delivery device of Example 2, where the scale bar is 400 μm in FIG. 27A and 50 μm in FIG. 27B;

FIG. 28 is a graph depicting the in vitro pulsatile PTH release profiles from the pulsatile delivery device (of Example 2) with 50 μm thick SA:CPP:PEG=80:20:2 isolation layers;

FIG. 3I illustrates, in black and white, the representative μCT reconstruction of mouse calvarial defects treated with the pulsatile PTH delivery device of Example 2, the continuous delivery device of Example 2, a pulsatile BSA control device of Example 2, and a PTH injection;

DETAILED DESCRIPTION

Figure 3:
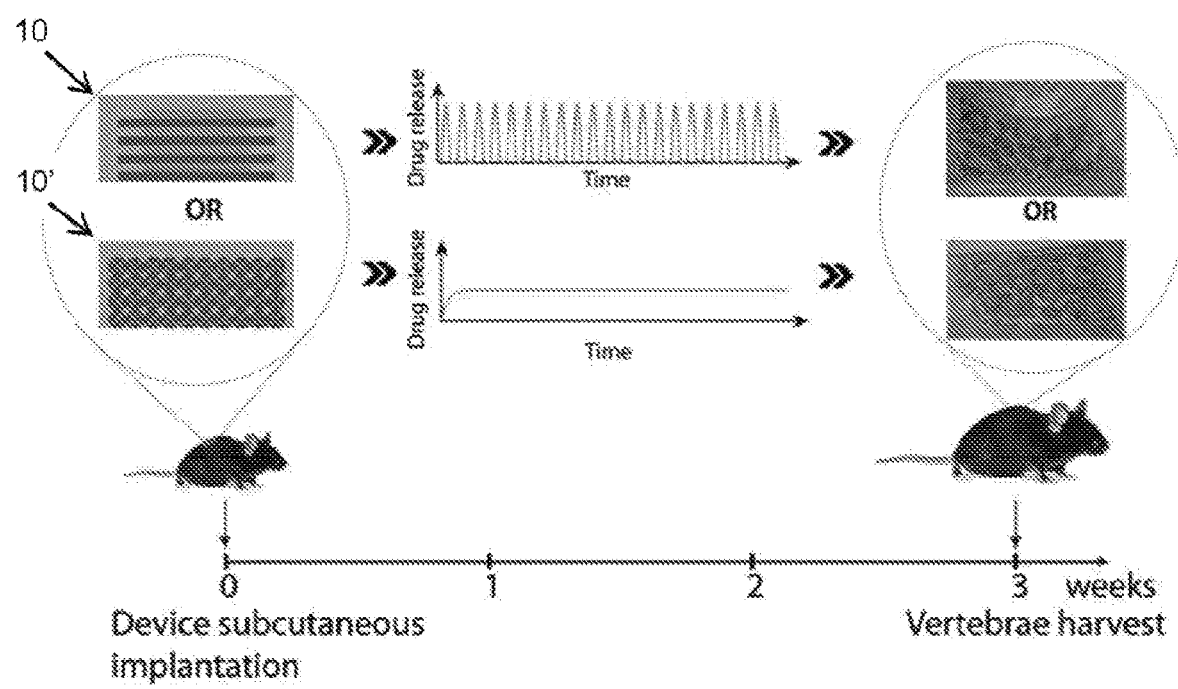
FIG. 3 is a schematic depiction of the experimental design for Example 1 disclosed herein.

Some examples of the delivery devices disclosed herein are pulsatile delivery devices, while others are continuous delivery devices. The continuous delivery devices are able to continuously release a drug (or other substance) over a controllable duration or time period. The pulsatile delivery devices enable a large number of controlled release pulses over a relatively long duration (e.g., 21 days) compared to other controlled release devices (e.g., 4 days). The pulsatile delivery device may be particularly useful for the long-term and preprogrammed delivery of PTH in order to systemically strengthen bone and activate local bone regeneration (i.e., promote bone growth). This pulsatile device may be suitable for treating various conditions of bone loss, without the burden of daily injections or secondary surgeries.

The method disclosed herein for making examples of the pulsatile delivery device utilizes an electrostatic assisted layer-by-layer stacking technique. Opposite charges generated on the stacked layers improve the adhesion between the layers, and reduce or eliminate air gaps between the layers. This method enables a large number of controlled release layers to be incorporated into the device, which improves the pulsatile release duration of the device.

Referring now to FIG. 1, an example of the method for making an example of the pulsatile delivery device 10 is depicted. The method for making the pulsatile delivery device 10 generally includes, generating one type of charges on a polymeric layer; generating charges opposite the one type of charges on a delivery layer, the delivery layer including a film forming material and a predetermined substance dispersed throughout the film forming material; placing the charged polymeric layer and delivery layer in contact to form a bi-layer structure; forming a stack with at least two bi-layer structures so that the polymeric layers and the delivery layers are alternating throughout the stack; and sealing the stack so that one of the polymeric layers remains exposed. The resulting pulsatile delivery device 10 includes alternating polymeric layers 12 and delivery layers 14, the latter of which include the substance to be controllably delivered to a patient.

The polymeric layers 12 are isolation layers, in part because they separate the delivery layers 14 from one another in the delivery device 10. In an example, the polymeric layers 12 are a two-component copolymer of a sebacic acid anhydride precursor and a 1,3-bis(carboxyphenoxy) propane anhydride precursor. In another example, the polymeric layers 12 are a three-component copolymer of a sebacic acid anhydride precursor, a 1,3-bis(carboxyphenoxy) propane anhydride precursor, and a poly(ethylene glycol) anhydride precursor. Examples of these copolymers and methods of forming the same are discussed in U.S. patent application Ser. No. 11/739,757, filed on Apr. 25, 2007 (U.S. Publication No. 2007/0249536), incorporated by reference herein. The PEG segments are incorporated into two-component polyanhydride copolymers, at least in part, to modulate the erosion rate and to improve processing properties of the polymeric layers 12. It is believed that the three-component polyanhydride copolymers retain the surface erosion characteristics of the two-component polyanhydride, while increasing the erosion rate. With increasing PEG content, the polyanhydride erosion rate increases. Without being bound to any theory, it is believed that the structural tunability of such polyanhydrides will advantageously enable a broad range of lag times (between substance release) and various device 10 sizes.

A weight ratio of the sebacic acid anhydride precursor to the 1,3-bis(carboxyphenoxy) propane anhydride precursor ranges from about 50:50 to about 90:10; and in an alternate example, ranges from about 95:5 to about 5:95. In a further example, the weight ratio of the sebacic acid anhydride precursor to the 1,3-bis(carboxyphenoxy) propane anhydride precursor is about 80:20. The poly(ethylene glycol) anhydride precursor may range from 0% to about 25% with respect to a total molar amount of the sebacic acid anhydride precursor and the 1,3-bis(carboxyphenoxy) propane anhydride precursor. In an example, the three-component polyanhydride copolymer includes the poly(ethylene glycol) anhydride precursor in an amount ranging from about 1% to about 10% with respect to a total molar amount of the sebacic acid anhydride precursor and the 1,3-bis(carboxyphenoxy) propane anhydride precursor.

It is to be understood that some examples of the copolymers may have different molecular weight PEGs incorporated therein as hydrophilic segments. Generally, the poly(ethylene glycol) anhydride precursor may be formed from PEGs having a number average molecular weight ranging from about 100 to about 10,000 (e.g., PEG100 to PEG10,000).

Other examples of suitable polymeric layers 12 include natural or synthetic degradable polymers, proteins, polysaccharides, hydrocarbon polymers, artificial proteins, and/or combinations thereof. Specific examples include poly(lactide-co-glycolide) (PLGA), polyglycolic acid (PGA), poly(L-lactic acid) (PLLA), polyanhydrides, poly(ortho esters), polycaprolactone, poly(hydroxy butyrate), poly(phosphoesters), poly(propylene fumarate), polyphosphazenes, polycarbonates, polyurethane, copolymers thereof, and/or combinations thereof.

To form the layers 12, the selected polymer(s) is/are heated until melted. The polymeric melt is then compressed into films of a desirable thickness and cooled down (e.g., to room temperature). It is to be understood that the composition and/or thickness selected for each of the layers 12 depends, at least in part, on the desirable release characteristics (lag time and release pattern) for the device 10. A single large polymeric layer 12 may be made, and then divided into any desirable shape for incorporation into the delivery device 10.

The delivery layer 14 including the substance may be formed by mixing the substance with a film forming material to form a solution, and casting the solution onto a removable or sacrificial substrate. Examples of the removable/sacrificial substrate include salt (e.g., sodium chloride, magnesium chloride, etc.), polysaccharides (e.g., fructose, galactose, glucose, lactose, maltose, and sucrose), paraffin, or calcium carbonate. In an example, the concentration range of the solution used to form the delivery layer 14 ranges from about 0.01 ng substance/ml film forming material to about 100 μg substance/ml film forming material.

Examples of the substance (in the delivery layer 14) include drugs (e.g., chemotherapy drugs, such as doxorubicin, cisplatin, carmustine, etc.), vaccines, proteins, peptides, growth factors, hormones (e.g., parathyroid hormone (PTH), luteinizing hormone release hormone (LHRH), 17β-estradiol, estriol, progesterone, testosterone, cortisol, insulin, etc.), nucleic acids (e.g., DNAs, RNAs, etc.), other biological molecules, non-biological molecules, and combinations thereof. Some specific examples of the substance are selected from the group consisting of chemokine ligand 2, chemokine ligand 7, interleukin 4, interleukin 13, transforming growth factor—beta (TGF-β), fibroblast growth factor (FGF), vascular endothelial growth factor (VEGF), platelet derived growth factor (PDGF), chemoattractant, bone morphogenetic protein (BMP), botulinum toxin, derivatives thereof, and combinations thereof. Still other examples of the substance include steroids (e.g., dexamethasone), antimicrobials, and other small molecules and/or additives, such as, ascorbic acid, β—glycerol phosphate, etc.

Examples of the film forming material may be selected from natural or synthetic hydrophilic polymers, natural or synthetic amphophilic polymers, proteins, polysaccharides, hydrocarbon polymers, lipids, artificial proteins, and/or combinations thereof. More specific examples include alginate, PEG, collagen, gelatin, hyaluronic acid, starch, glycogen, cellulose, caragena, dextran, chitin, chitosan, pectin, heparin, heparan sulfate, copolymers thereof, small water-soluble molecules (such as sugars, salts), and combinations thereof. It is believed that alginate may be particularly suitable as a carrier for the selected substance, in part, because of its biocompatibility and suitable processing properties.

The cast solution is dried (e.g., freeze-dried or dried by some other suitable technique) to form the delivery layer 14. The delivery layer 14 may be removed from the substrate and divided into any desirable shape for incorporation into the delivery device 10. The cast solution may be dried, e.g., by freeze-drying or by some other suitable drying technique. The sacrificial substrate may then be removed from the formed delivery layer 14.

The thickness and substance content of the delivery layer 14 may be selected, at least in part, on the desirable amount of substance to be released and the release time.

Each of the polymeric layers 12, 12', etc. may have an area that is equal to or larger than an area of each of the delivery layers 14, 14', etc. This configuration decreases or eliminates the risk that indirectly adjacent delivery layers 14, 14', 14", 14'" in the delivery device 10 will come into contact with one another, and thus substantially prevents leakage of the substance between the layers 14, 14', 14", 14'". It is to be understood that indirectly adjacent delivery layers 14, 14', 14", 14'" are delivery layers e.g., 14 and 14', 14' and 14", etc. that would be in direct contact with one another if the polymeric layer 12, 12' positioned therebetween was not present or removed.

In the method shown in FIG. 1, charges of one type (e.g., positive charges) are generated on the polymeric layer 12, and charges opposite to the charges of the one type (e.g., negative charges) are generated on the delivery layer 14. The charges may be generated on one or both surfaces of the layers 12, 14, on a portion of one or both surfaces of the layers 12, 14, or the entire layer 12, 14 may be charged as a result of the methods disclosed herein. Any film 13 that has a strong tendency to gain electrons may be used to generate the positive charges. In an example, a polytetrafluorethylene (PTFE) film (e.g., TEFLON®, available from The Chemours Co.) may be rubbed on the surface(s) of the polymeric layer 12 to form the positive charges. Other examples of suitable films 13 that may be used to form the positive charges include polyvinyl chloride (PVC), polyethylene (PE), polypropylene (PP), or polystyrene (PS). Any film 15 that has a strong tendency to lose electrons may be used to generate the negative charges. In an example, a glass slide may be rubbed on the surface(s) of the delivery layer 14 to form the negative charges. Other examples of suitable films 15 that may be used to form the negative charges include polymethyl methacrylate (PMMA), nylon (polyamide), fur, silk, or celluloid nitrate.

The charged layers 12, 14, or charged surfaces of the respective layers 12, 14 may then be brought or placed into contact with one another. The opposite charges are electrostatically attracted to each other, which enables close contact between the layers 12, 14 and substantially eliminates air gaps between the layers 12, 14. The electrostatically attracted layers 12, 14 form a bi-layer structure 16.

Several bi-layer structures, for example 16, 16', 16", 16'" may be positioned adjacent to one another to form a stack 18. The bi-layer structures 16, 16', 16", 16'" are positioned so that the polymeric layers 12 and the delivery layers 14 are alternating throughout the stack 18. As such, the delivery layer of one bi-layer structure may be in contact with the polymeric layer of another bi-layer structure. As examples, the polymeric layer 12' of bi-layer structure 16' is in contact with the delivery layer 14 of the bi-layer structure 16, and the delivery layer 14' of the bi-layer structure 16' is in contact with the polymeric layer 12" of bi-layer structure 16".

When stacking the bi-layer structures 16, 16', 16", 16'", the exposed surfaces of some of the layer(s) 12 and/or 14 may be exposed to the respective process for generating positive or negative charges thereon. These charges may enhance the attraction between the bi-layer structures 16, 16', 16", 16'". For example, before the bi-layer structures 16 and 16' are placed into contact, the surface of the polymeric layer 12' of bi-layer structure 16' that is to contact the delivery layer 14 of the bi-layer structure 16 may have positive charges generated thereon, and the surface of the delivery layer 14 of the bi-layer structure 16 that is to contact the polymeric layer 12' of bi-layer structure 16' may have negative charges generated thereon.

In another example of the method (not shown), the opposed surfaces of all of the layers 12, 14, 12', 14', etc. that are to be included in the stack 18 may be exposed to the respective charge generation process. As such, both surfaces of each layer 12, 14, 12', 14' etc. are charged. The charged layers 12, 14, 12', 14', etc. may then be stacked one by one in the alternate configuration (e.g., polymeric layer 12, delivery layer 14, polymeric layer 12', delivery layer 14', etc.) to form the stack 18.

After the stack 18 is formed, the stack 18 may be sealed with an elastic sealant material 20 so that the outermost polymeric layer 12 remains exposed (i.e., not covered by the elastic sealant layer 20). The elastic sealant material 20 is a slow biodegrading polymer compared to the polymeric layers 12 and the film forming material of the delivery layers 14. This ensures that the substance is uni-directionally released from one end E of the device 10 (e.g., in a pulsed fashion as the layers 12, 14, 12', 14" sequentially degrade). Examples of the slower degrading elastic sealant material 20 include polycaprolactone (PCL), PCL copolymers (e.g., PGCL (poly(glycolide-co-caprolactone)), PLCL poly(lactide-cocaprolactone)), PGS (Poly(glycerol sebacate)), PU (Polyurethane), Poly(diol citrate), biopolymers (such as elastin or elastin-like polypeptides), etc. Some of the listed polymeric layer 12 materials are also suitable for forming the elastic sealant material 20 (e.g., polyurethane). However, when this type of material is selected for the polymeric layer(s) 12, 12', etc., it is to be understood that this same type of material will not be selected for the elastic sealant material 20. For example, in a device 10 that includes polyurethane polymeric layers 12, 12', etc., polyurethane will not be selected as the elastic sealant material 20, but rather, a material that degrades slower than the polyurethane will be selected as the elastic sealant material 20.

In one example, the elastic sealant material 20 is coated on one end of the stack (e.g., on the outermost delivery layer 14'", opposed to the end E) and on an outer edge of the stack 18. The outer edge of the stack 18 may be made up of the exposed ends/sides (i.e., along the thickness) of each layer 12, 14, 12', 14', etc. In another example, the stack 18 may be built up on an elastic sealant layer 22 (shown in phantom), and the elastic sealant material 20 is coated on the outer edge of the stack 18. The elastic sealant layer 22 may be formed of the same material as the elastic sealant material 20.

Coating the elastic sealant material 20 may be accomplished using any suitable deposition technique, such as casting, spraying, sputtering, spin-coating, CVD (chemical vapor deposition), etc.

As an example of the sealing process, a solution of the elastic sealant material 20 may be formed. One example of the solution is 35% w/v polycaprolactone dissolved in dichloromethane (DCM). The solution may then be cast on the outer edge of the stack 18 or on the outermost delivery layer 14''' and on the outer edge of the stack 18. This forms a construct that is then subjected to vacuum. In an example, vacuum may be performed in 10 inches of mercury (10 in Hg) for about 1 minute to allow the sealant solution to penetrate and seal the gap between the differently sized layers 12, 14, 12', 14', etc. Casting and exposure to vacuum may be repeated a desirable number of times to build up the sealant. When the final layer of elastic sealant material 20 is cast and subjected to vacuum, the construct may be dried under vacuum (e.g., 20 in Hg) for a time period ranging from about 8 hours to about 24 hours.

As such, in an example, the pulsatile delivery device 10 includes a stack of at least two bi-layer structures 16, 16', each bi-layer structure 16, 16' including: a delivery layer 14 including a film forming material and a predetermined substance dispersed throughout the film forming material; and a polymeric layer 12 electrostatically attached to the delivery layer; and a sealant 20 partially surrounding the stack so that one of the polymeric layers 12 of the stack is exposed.

The example pulsatile delivery device 10 shown in FIG. 1 includes four bi-layer structures 16, 16', 16'', 16''' stacked up. In some examples, at least ten bi-layer structures 16, 16', 16'', 16''' are stacked up. In still other examples, as many as twenty-one (21) bi-layer structures may be stacked within a single device 10. The 21 bi-layer structure may be particularly suitable for 3 week osteoporosis treatment. The number of bi-layer structures 16, 16', 16'', 16''' may be increased or decreased depending upon the application in which the device 10 is to be used.

It is to be understood that the delivery layers 14, 14', 14'', 14''' including the substance may be the same or different throughout the device 10. For example, the substance loading may be lower in some layers 14, 14' than in others 14'', 14''', or the type of substance may be different in two or more layers 14, 14', 14'', 14'''. In an example, the amount of substance loaded in each layer 14, 14', 14'' is the same as or lower than the substance loading in the layer 14', 14'', 14''' immediately, but indirectly adjacent (and further from the end E), in part, to overcome the potential adsorption and diffusive losses of the released substance in upper (e.g., closer to the end E) layers 14, 14', 14''.

Referring now to FIG. 2, an example of the method for making an example of the continuous delivery device 10' is depicted. The continuous delivery device 10' includes a plurality of microspheres 24, which include the substance 26 to be controllably delivered to a patient encapsulated in a biodegradable sphere 28.

The substance 26 may be any of the substances previously described for the delivery layers 14, and the biodegradable sphere 28 may be any of the materials previously described for the polymeric layers 12. As examples, the biodegradable sphere 28 may be a poly(ortho ester) or a heteropolymer of anhydrides of each of sebacic acid (SA), 1,3-bis (p-carboxyphenoxy) propane (CPP), and poly(ethylene glycol) (PEG).

The microspheres 24 may have micron scale dimensions (e.g., from 1 μm to about 100 μm). In some examples the spheres 24 are smaller, having nanoscale dimensions ranging from about 1 nm to about 1000 nm. Formation of the biodegradable sphere 28 and encapsulation of the substance 26 may be performed via a double emulsion technique, such as a water-in-oil-in-water double emulsion (shown in FIG. 2). Sphere 28 formation and substance 26 encapsulation may also be performed, for example, by a simple emulsion technique, extrusion, phase separation, spray-drying, etc.

In the method shown in FIG. 2, the substance 26 is dissolved into water to form the water phase 26'. An agent that protects the substance 26 from denaturing during the emulsion process may also be included in the water phase 26'. Examples of suitable agents include any of the hydrophilic film forming materials of the delivery layers 14, such as alginate, PEG, collagen, gelatin, hyaluronic acid, starch, glycogen, cellulose, caragena, dextran, chitin, chitosan, pectin, heparin, heparan sulfate, copolymers thereof, small water-soluble molecules (such as sugars, salts), and combinations thereof. These agents may form drug-loaded hydrophilic domains distributed throughout the microspheres 28. An oil phase 28' is also prepared with a suitable biodegradable material and a solvent.

The water phase 26' is emulsified in the oil phase 28' to form the first (or primary) water-in oil (w/o) emulsion. Emulsification may take place with a probe sonicator at 10W (Virsonic 100, Gardiner, N.Y.) or with another suitable mechanism. The primary w/o emulsion may then gradually be added into another aqueous solution (e.g., an aqueous polyvinyl alcohol solution) under sonication to form the second (or secondary) water-in-oil-in-water (w/o/w) emulsion. The resulting secondary emulsion may be magnetically stirred at room temperature for a suitable time to evaporate the solvent. The microspheres 24 may then be collected by centrifugation and washed multiple times with water and freeze dried.

A plurality of the microspheres 24 may then be compressed into a disk 30, as shown in FIG. 2. In an example, the compression pressure may range from about 100 PSI to about 4,000 PSI. Increased compression pressure may lead to a small decrease in the release rate of the substance 26 from the microspheres 24, and thus lower compression pressures may be desirable in some instances. The disk 30 includes the substance-encapsulated polymeric microspheres 24 compressed together.

While an elastic sealant material 20 is shown in FIG. 2, the disk 30 may be used without the elastic sealant material 20. This may be desirable when the surface area of the end E' and the end opposite the end E' is substantially larger than the surface area of the side(s) (e.g., cylindrical side).

As shown in FIG. 2, the disk 30 may be sealed with the elastic sealant material 20 so that at least one surface (e.g., end E') of the disk 30 remains exposed (i.e., not covered by the elastic sealant layer 20). In the example shown in FIG. 2, the one end E' is not coated with the elastic sealant material 20, and the opposite end and the cylindrical side(s) are coated with the elastic sealant material 20. This ensures that the substance 26 is uni-directionally released from one end E' of the device 10' (e.g., in a continuous fashion as the biodegradable spheres 28 degrade). In another example, the cylindrical side(s) are coated with the elastic sealant material 20, but the end E' and the opposite end remain uncoated. This ensures that the substance 26 is bi-directionally released from the opposed ends of the device 10' (e.g., in a continuous fashion as the biodegradable spheres 28 degrade). The elastic sealant material 20 may be any of the materials previously described, and may be a slow biodegrading polymer compared to the biodegradable sphere 28. Examples of the slower degrading elastic sealant material 20 include polycaprolactone (PCL), PCL copolymers (e.g., PGCL (poly(glycolide-co-caprolactone)), PLCL poly(lactide-cocaprolactone)), PGS (Poly(glycerol sebacate)), PU (Polyurethane), Poly(diol citrate), biopolymers (such as elastin or elastin-like polypeptides), etc. The elastic sealant material 20 may also be a non-degradable polymer, depending upon the application in which the device 10' is to be used.

In the example shown in FIG. 2, the elastic sealant material 20 may be coated in any manner previously described in reference to FIG. 1. In one example, the elastic sealant material 20 is coated on one end of the disk 30 (e.g., opposed to the end E') and on an outer edge of the disk 30. The outer edge of the disk 30 may be made up of the exposed microspheres 24 that are positioned at the outermost portion along the thickness of the disk 30. In another example, the disk 30 may be positioned on an elastic sealant layer 22 (shown in phantom), and the elastic sealant material 20 is coated on the outer edge of the disk 30. The elastic sealant layer 22 may be formed of the same material as the elastic sealant material 20.

Coating the elastic sealant material 20 may be accomplished using any suitable deposition technique, such as casting, spray coating, sputtering, spin-coating, CVD (chemical vapor deposition), etc.

As an example of the sealing process, a solution of the elastic sealant material 20 may be formed. One example of the solution is 35% w/v polycaprolactone dissolved in dichloromethane (DCM). The solution may then be cast on the outer edge of the disk 30 or on one surface (e.g., at end E') and on the outer edge of the disk 30. This forms a construct that is then subjected to vacuum. Vacuum may be performed in 10 inches of mercury (10 in Hg) for about 1 minute to allow the sealant solution to penetrate and seal the gap between the differently sized layers 12, 14, 12', 14', etc. Casting and exposure to vacuum may be repeated a desirable number of times to build up the sealant. When the final layer of elastic sealant material 20 is cast and subjected to vacuum, the construct may be dried under vacuum (e.g., 20 in Hg) for a time period ranging from about 8 hours to about 72 hours).

In an example, the continuous delivery device includes a disk 30 including a plurality of substance-encapsulated polymeric microspheres 24 compressed together. In another example, an elastic sealant partially surrounds the disk 30 so that at least one surface of the disk 30 is exposed.

Examples of both of the devices 10, 10' disclosed herein are capable of degrading and being absorbed in vivo, and thus may be implanted into a patient. Since these example devices are degradable and absorbable, there is no need for a retraction or extraction procedure, such as surgical removal of the devices 10, 10'. Such devices 10, 10' may be suitable for systemic and for local therapies. As examples, the devices 10, 10' disclosed herein may be configured for osteoporosis treatment, bone regeneration, defective tissue treatment, ovulation induction, treatment of vasomotor symptoms, treatment of urogenital symptoms, endometrial hyperplasia treatment, allergic rash treatment, eczema treatment, and/or the like, and/or combinations thereof.

Figure 24:
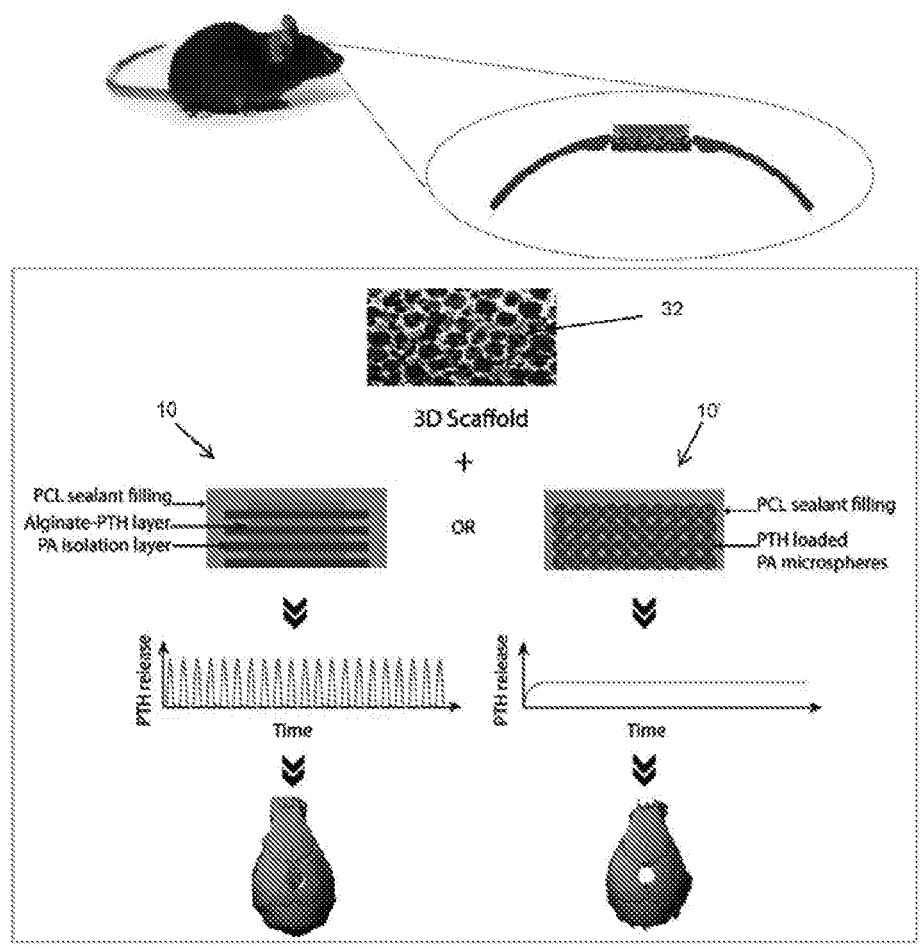
FIG. 24 is a schematic depiction of the experimental design for Example 2 disclosed herein.

The devices 10, 10' may be used with or without a support structure (shown as reference numeral 32 in FIG. 24). The support structure 32 may be desirable when the device 10, 10' is used for bone repair, and the support structure may be implanted adjacent to the end E, E' of the device 10, 10' in the bone defect that is to be repaired. The support structure 32 may be cell-free.

An example of the support structure 32 includes a scaffold formed of a plurality of nano-fibers aggregated together and pores defined between at least some of the nano-fibers. The nano-fibers mimic the structure of the extracellular matrix (ECM), and thus may promote tissue regeneration. Additionally, the scaffold likely increases gene delivery vehicle-loading efficiency, decreases the amount of degradation product, facilitates cell-cell and cell-matrix interactions, and provides an easy path for nutrient and metabolic waste transfer, which together synergistically enhance tissue regeneration and integration with the host. Other examples of suitable support structures 32 include non-fibrous porous scaffolds, hydroxyapatite, beta-TCP, polymer particles, hydrogels (e.g., made from, for example, one or more polymers and/or monomers, including polyethylene glycol diacrylate, alginate, acrylic acid, acrylamide, methylene bisacrylamide, etc.).

One specific example of the scaffold is referred to as a nanofibrous scaffold. The nanofibrous scaffold is characterized as a multi-level porous structure with regular spherical macro-scale pores (ranging from about 250 µm to about 425 µm in diameter), micro-scale interpore openings (i.e., openings that connect one macro-scale pore to another macro-scale pore) ranging from about 10 µm to about 100 µm, and spaces (less than 2 µm in diameter) between the nanofibers. While the pores of the scaffold are on the macro-scale or smaller, the scaffold itself has larger dimensions. For example, the thickness of the scaffold may be 0.5 mm or more, and the length and/or width of the scaffold may be 2 mm or more. For another example, the thickness of the scaffold may be 1 mm or more, and the length and/or width of the scaffold may be 3 mm or more. In another example, the polymer scaffold may have a porous structure and solid walls, rather than fibrous walls.

The support structure 32 may be formed of any of the polymeric materials previously described for the polymeric layers 12, and may be formed via any suitable technique. As an example, the nanofibrous scaffold may be formed via a combination of phase separation and template (e.g., sugar) leaching techniques or emulsification techniques in which glycerol is added to the polymer solution and serves as a template for forming the pores.

To further illustrate the present disclosure, examples are given herein. It is to be understood that these examples are provided for illustrative purposes and are not to be construed as limiting the scope of the present disclosure.

EXAMPLES

Example 1

This example was performed to examine the distinct PTH delivery patterns and their therapeutic effects on systemically strengthening bone in a mouse model. The experimental design is shown in FIG. 3. The pulsatile delivery device 10 and the continuous delivery device 10' were subcutaneously implanted in mice, and bones and serum were collected three weeks later to examine the systemic effects of the two PTH release modes on bone.

Pulsatile Delivery Device

Multi-pulse Bovine serum albumin (BSA, a control protein) or PTH delivery devices were formulated. The devices was made of alternating drug layers (substance layers 14)

and isolation layers (polymeric layers 12), and were formed via the method shown in FIG. 1.

Figure 4:
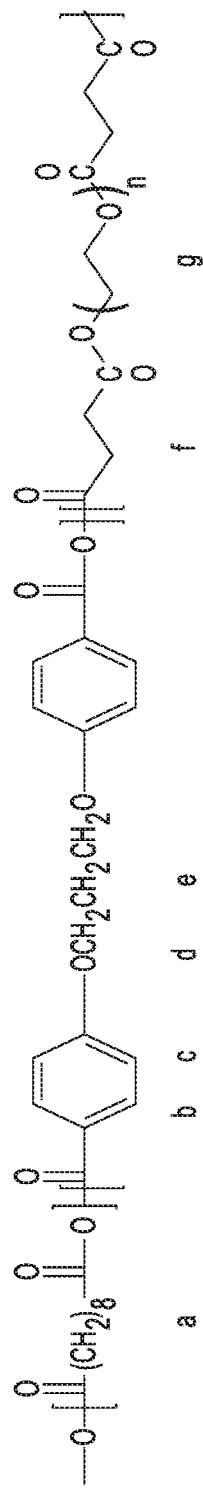
FIG. 4 is a Nuclear Magnetic Resonance (NMR) spectrum (400 MHz, $CDCl_3$) of a three-component polyanhydride copolymer formed from an anhydride of sebacic acid (SA), an anhydride of 1,3-bis (p-carboxyphenoxy) propane (CPP), and an anhydride of poly(ethylene glycol) (PEG)
Figure 4:
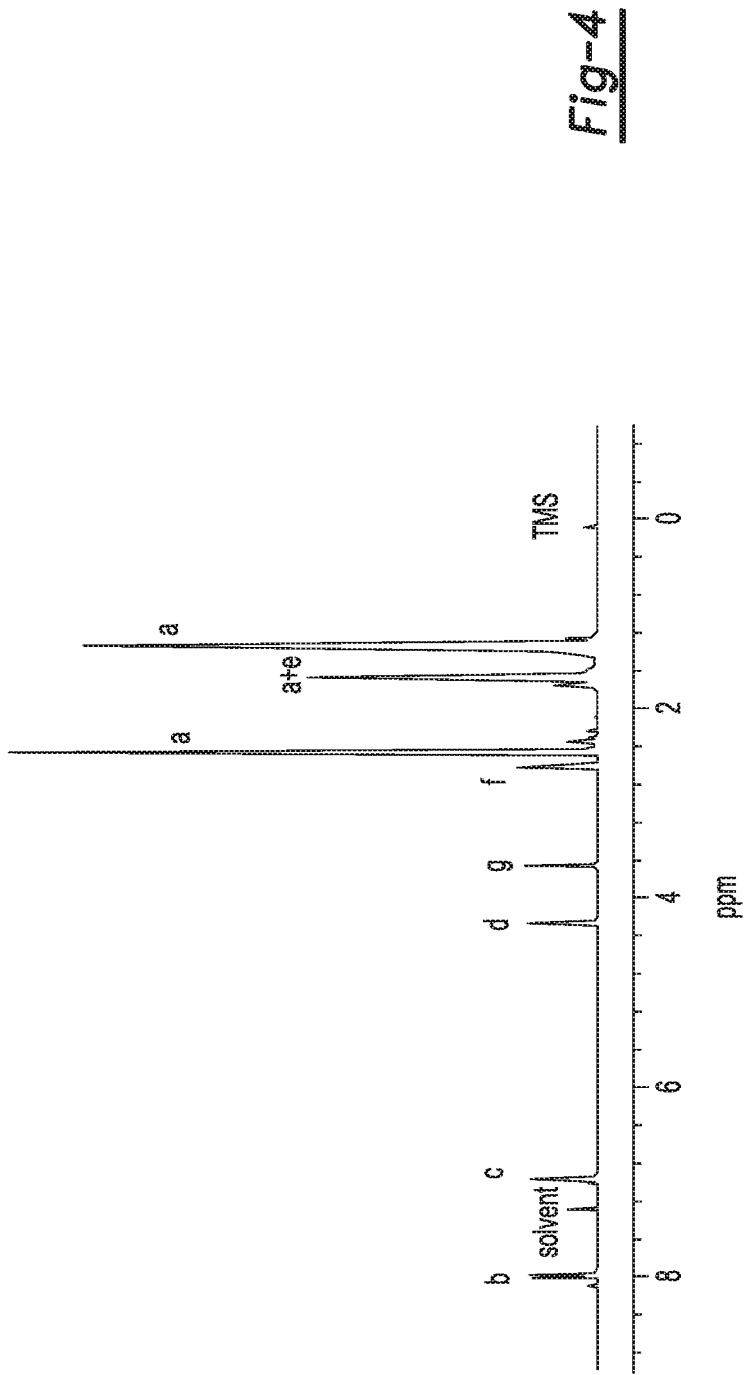

The isolation layers were made of three-component polyanhydride copolymers (PA copolymer), which are biocompatible, and biodegradable through surface erosion. The PA copolymer was composed of anhydrides of sebacic acid (SA), 1,3-bis (p-carboxyphenoxy) propane (CPP), and poly (ethylene glycol) (PEG, Mw=1000), and was formed by condensation polymerization. The PEG segments were incorporated into the copolymer to increase the hydrophilicity and improve the hydrolytic degradation. Nuclear Magnetic Resonance (NMR) spectroscopy confirmed the successful synthesis of the three-component polyanhydride copolymer, as the spectrum showed a set of typical poly (SA-CPP-PEG) peaks (see FIG. 4, PEG (3.4-3.8 ppm), CPP (6.9 and 8.0 ppm), and SA (1.4-2.2 ppm)).

Figure 5A:
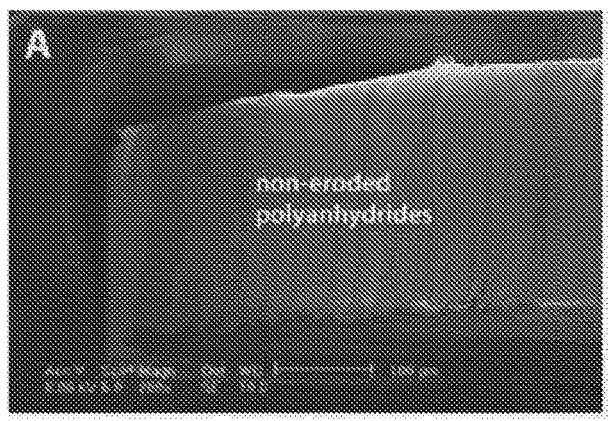
FIGS. 5A through 5D are Scanning Electron Microscopy (SEM) micrographs of an untreated three-component polyanhydride copolymer (5A), and polyanhydride copolymers with different compositions (SA:CPP:PEG=80:20:0 (5B), SA:CPP:PEG=80:20:2 (5C), SA:CPP:PEG=80:20:8 (5D)) after erosion in 0.1M phosphate buffered saline (PBS) at 37° C. for 12 hours.
Figure 5B:
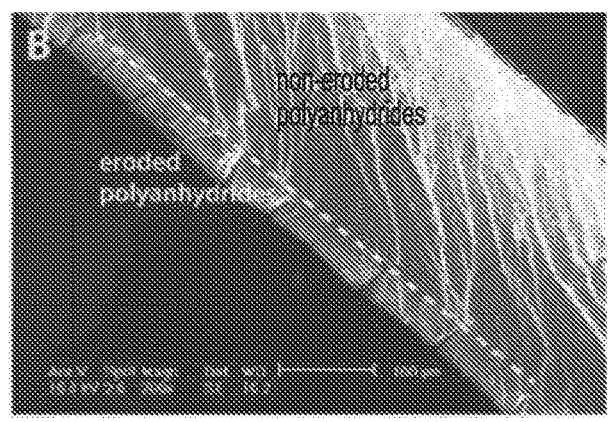
Figure 5C:
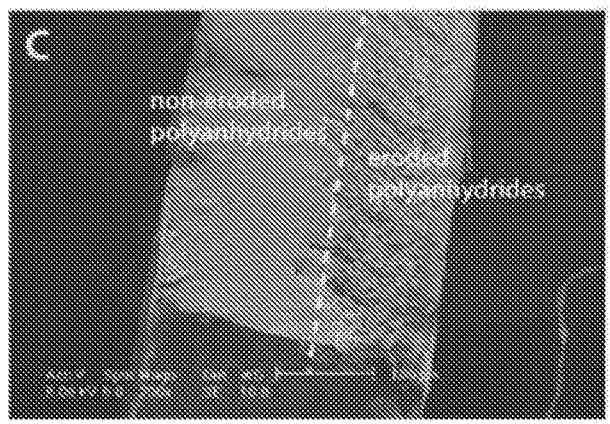
Figure 5D:
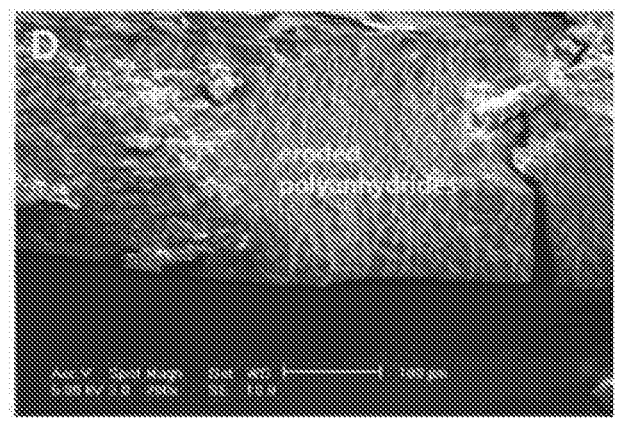

Prior to forming the isolation layers, the degradation of the polyanhydride copolymers was analyzed. More specifically, Scanning Electron Microscopy (SEM) was used to examine the copolymer degradation. The examined copolymers included SA:CPP:PEG in ratios of 80:20:0 (a comparative copolymer), 80:20:2, and 80:20:8. Untreated copolymers were stored under vacuum. Erosion was accomplished by exposing the copolymers to 0.1M phosphate buffered saline (PBS) at 37° C. for 12 hours. The cross-section of the un-eroded polymer was uniform (FIG. 5A), while there were evident pores in eroded portions of the treated samples (see FIGS. 5B through 5D). The erosion front moving with time was an indication of surface erosion. The polyanhydride copolymer containing more PEG segments exhibited a faster erosion rate than those containing fewer PEG segments. It was also observed that the eroded surface roughness increased with increasing PEG content of the copolymer. The polyanhydride copolymers containing PEG retained the surface erosion properties of the comparative copolymer, while imparting a large range of a tunable erosion rate.

The dissolution time of the surface erosion polymer layer is generally proportional to the thickness of the layer. Therefore the thickness of each isolation layer may be adjusted to achieve desired time intervals between adjacent pulses of drug release from the formed device.

Based on the effect of increasing PEG content and layer thickness, the pulsatile release profile was preprogrammed by modulating the chemical composition and physical thickness of the isolation layers. More specifically, varying the chemical composition and thickness of the isolation layers enabled the release kinetics to be programmed to target the entire 3-week therapeutic window. For the composition, the polyanhydride copolymer including 80 SA: 20 CPP: 2 PEG was used. The three-component polyanhydride copolymer was melted and compressed into layers of various thicknesses (50 µm, 100 µm and 200 µm) with error ≤10 µm. The PA copolymer layers were punched into disks of desired size (3 mm in diameter) to form the isolation layers.

BSA or PTH (1-34) (Bachem Bioscience Inc., Torrance, Calif.) was mixed with alginate in a 1:1.67 weight ratio to form the drug layers. Alginate was used as the drug/protein carrier because of its biocompatibility and processibility. The mixture was dissolved in distilled water and the solution was cast into a film and freeze-dried for 1 day. The alginate-BSA and alginate-PTH films were then punched into disks of desired size (2 mm in diameter) to form the drug layers.

The 2 mm drug layers were designed to be smaller than the 3 mm diameter isolation layers to prevent possible contact between adjacent drug layers, which could lead to the leakage of drug between layers.

Figure 6:
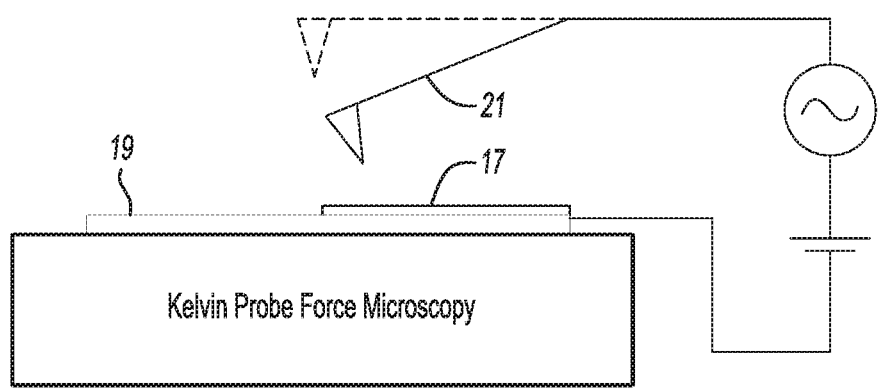
FIG. 6 is a schematic illustration of Kelvin probe force microscopy (KPFM) used to measure the surface potential of the isolation layer and the drug layer of Example 1.
Figure 7A:
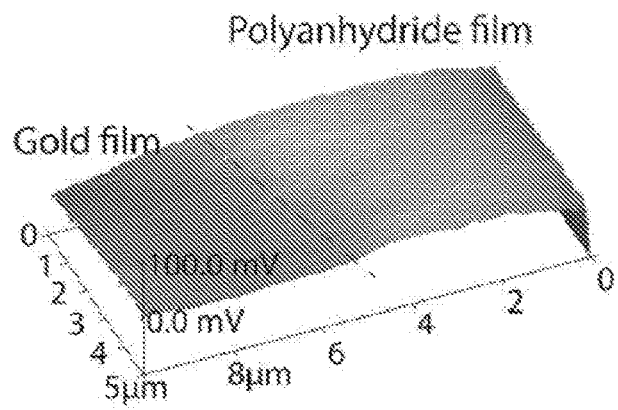
FIGS. 7A and 7B respectively illustrate the surface potential map (shown in black and white) and the potential difference between a gold substrate and the isolation layer of Example 1.
Figure 7B:
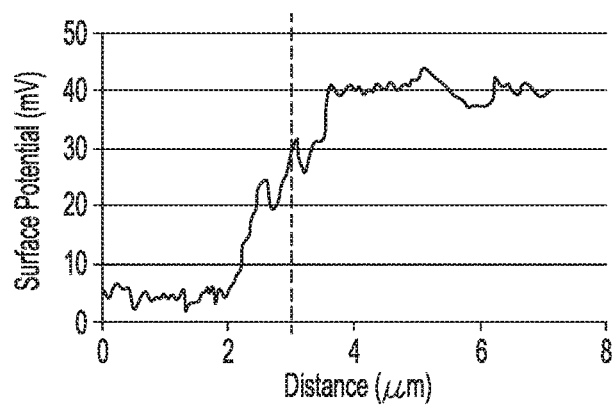
Figure 8A:
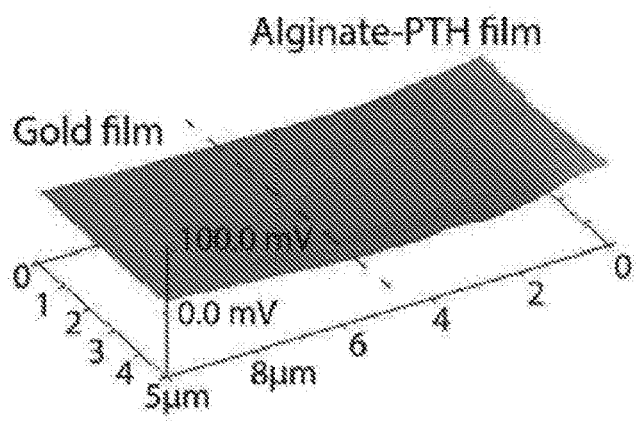
FIGS. 8A and 8B respectively illustrate the surface potential map (shown in black and white) and the potential difference between a gold substrate and the drug layer of Example 1.
Figure 8B:
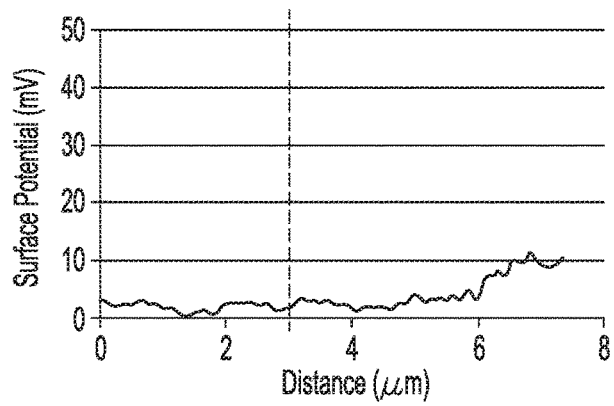

The surface potential of the isolation layer and the drug layer were examined using Kelvin probe force microscopy (KPFM, Bruker NanoMan AFM). A schematic illustration of the KPFM used to measure the surface potential of the layers is shown in FIG. 6. 10% w/v of a PA copolymer/DCM solution or an alginate-PTH aqueous solution was spin coated to form a sample film 17 of the isolation layer or the drug layer onto a gold substrate 19. The KPFM was equipped with a conductive tip (probe) 21 that was used to map the surface potential of the sample film 17 of the respective layers in tapping mode. The data was analyzed with the software (Nanoscope) equipped with the KPFM. The relative surface potentials of the two layers were calculated using the gold substrate 19 as reference (0 mV). It was found that the isolation layer was positive and the drug layer was nearly neutral. More particularly, the surface potential of the isolation layer (~40 mV) was about 6 times higher than the surface potential of the drug layer (~7-8 mV) (compare FIGS. 7A and 7B to FIGS. 8A and 8B). The intrinsic surface potential difference facilitated the generation of opposite electrostatic charges on the two layers.

Figure 9:
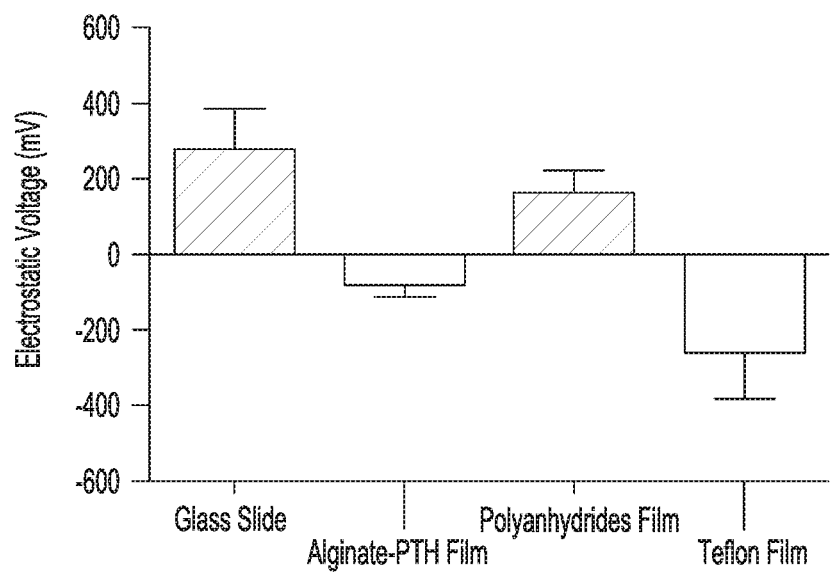
FIG. 9 is a graph illustrating the electrostatic potential (mV) of the isolation layer (labeled polyanhydrides film) and the drug layer (labeled alginate-PTH film) of Example 1 after respectively generating positive and negative charges thereon, and of the polytetrafluorethylene (TEFLON®) used to generate the positive charges and the glass slide used to generate the negative charges.

The isolation layers were rubbed with a TEFLON® film to generate positive surface charges and the drug layers (containing PTH or BSA) were rubbed with a glass slide to generate negative surface charges. The electrostatic voltages of the two different layers, as well as the TEFLON® film and the glass slide) were measured using a non-contact static meter (Electro-Tech Systems Static Meter Model 200). The results are shown in FIG. 9. The results indicated that opposite charges were generated on the isolation layer (i.e., polyanhydrides film) (about +160 mV) and the drug layer (alginate-PTH film) (about −80 mV).

One charged isolation layer and one charged drug layer (PTH for one device and BSA for a control device) were placed into contact. The oppositely charged layers were attracted to each other to form one bi-layer structure. 21 bi-layer structures were stacked up on a polycaprolactone (PCL) sealant layer (with the drug layer in direct contact with the PCL sealant layer), and the outermost layer of the stack was an isolation layer. A clamp was used to compress the multilayer structure/stack from the top and the bottom to ensure the close contact between layers. PCL was dissolved in DCM to form a 35% w/v viscous clean solution, and 50 µl of the PCL/DMC solution was carefully casted and coated onto the cylindrical side to form a construct. The outermost isolation layer was left exposed or unsealed, which ensured one-direction erosion (e.g., from the outermost isolation layer to the drug layer in direct contact with the PCL sealant layer) and thus unilateral drug release from the formed device. The construct was subject to vacuum (10 in Hg) for about 1 minute to allow the PCL to penetrate and seal the gaps between the isolation layers (which were created due to the difference in diameter between the isolation and drug layers). The sealing process was repeated 3 times and then the whole device was dried under vacuum (20 in Hg) for 3 days.

Figure 10:
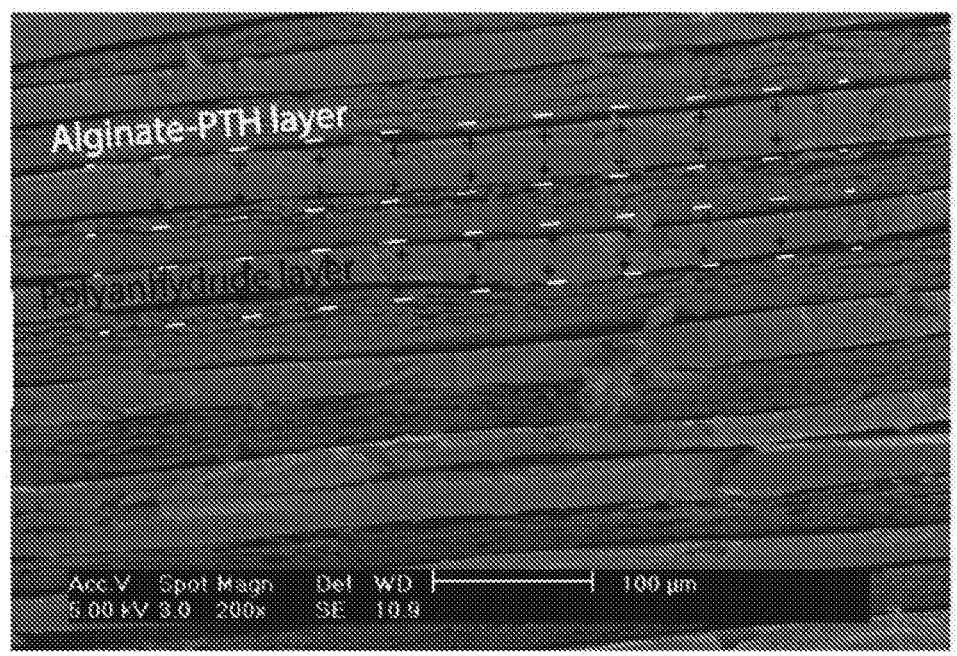
FIG. 10 is a cross-sectional SEM micrograph illustrating a portion of the pulsatile delivery device of Example 1.

The electrostatic attachment technique and the sealing technique enabled close contact between drug layers and isolation layers and eliminated air gaps. A cross-sectional SEM image (illustrating some of the stacked and sealed isolation and drug layers) of a portion of the pulsatile delivery device formed with the alginate-PTH drug layer is shown in FIG. 10. SEM images may be used to examine the cross-section of the electrostatically attached layers to confirm that air gaps have been removed. The air gap can also be calculated by subtracting each individual film's thickness (before being assembled into the device 10 disclosed herein) from the assembled device thickness.

The pulsatile delivery device formed with BSA was a control device.

Continuous Delivery Device

BSA and PTH continuous delivery devices were formulated. The continuous delivery devices were made of drug-encapsulated polyanhydride copolymer microspheres, and were formed via the double emulsion method shown in FIG. 2.

Figure 11A:
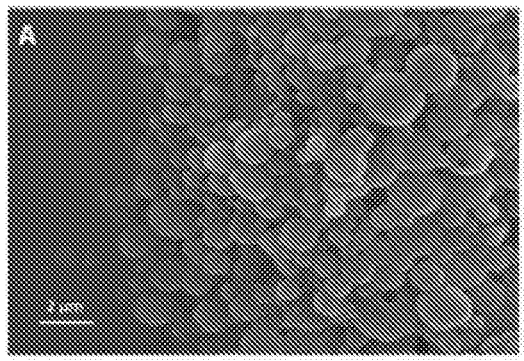
FIGS. 11A through 11D are SEM micrographs of untreated three-component polyanhydride copolymer particles (11A), and polyanhydride copolymer particles with different compositions (SA:CPP:PEG=80:20:0 (11B), SA:CPP:PEG=80:20:2 (11C), SA:CPP:PEG=80:20:10 (11D)) after erosion in 0.1M phosphate buffered saline (PBS) at 37° C. for 12 hours.
Figure 11B:
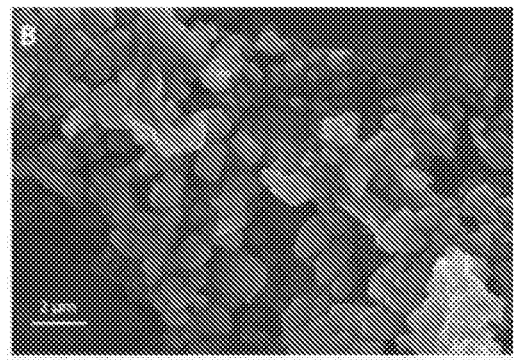
Figure 11C:
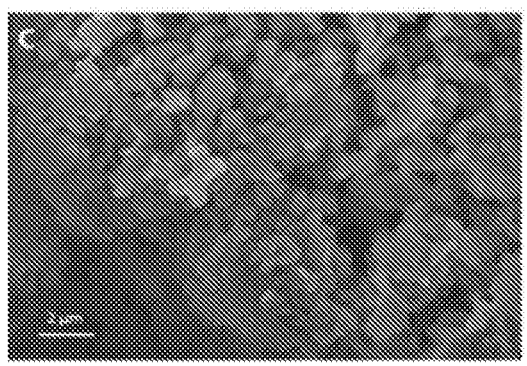
Figure 11D:
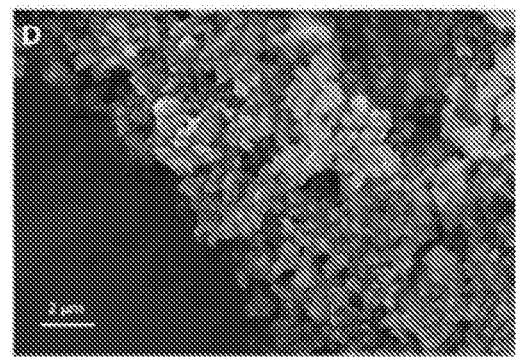

Polyanhydride copolymers including 80 SA: 20 CPP:0 PEG, 80 SA:20 CPP:2 PEG, and 80 SA:20 CPP:10 PEG were prepared via condensation polymerization. Prior to forming the drug-encapsulated microspheres, the degradation of the polyanhydride copolymers particles was analyzed. More specifically, Scanning Electron Microscopy (SEM) was used to examine the degradation. The examined copolymer particles were formed from monomer (SA:CPP:PEG) feed ratios of 80:20:0 (a comparative copolymer), 80:20:2, and 80:20:10. Untreated copolymer particles were stored under vacuum. Erosion was accomplished by exposing the copolymer particles to 0.1M phosphate buffered saline (PBS) at 37° C. for 12 hours. The images showed that the un-eroded copolymer particles were spherical in shape with smooth surfaces (FIG. 11A), and that the size of the particles decreased and the particles lost the spherical shape and fused together as they degraded in PBS (FIGS. 11B through 11D). Instead of being porous throughout the particles, which would likely lead to a burst drug release, the surface erosion property of the polyanhydride copolymers resulted in the degradation only on the surface, thus enabling the steady linear drug release that was observed from the drug-encapsulated microspheres (see in vitro results below). The degradation results illustrated that the release kinetics of the continuous delivery device could be modified by varying the chemical composition of the polyanhydride copolymer microspheres.

To form the drug-encapsulated polyanhydride copolymer microspheres, bovine serum albumin (BSA) or PTH was first dissolved in distilled water with 0.1 wt. % gelatin (which was used to prevent denaturation during the double emulsion) to form a drug solution. The drug solution was emulsified in a 10% w/v polyanhydride copolymer/dichloromethane (DCM) solution, using a probe sonicator at an output power of 10 W (Virsonic 100, Cardiner, N.Y.), for 10 seconds over an ice bath to form the water-in-oil (w/o) emulsion. The w/o emulsion was then gradually added into 20 ml of an aqueous polyvinyl alcohol (PVA) solution (1% w/v) under sonication at an output power of 20 W to form a water-in-oil-in-water (w/o/w) double emulsion. The double emulsion was stirred at room temperature for 3 hours to evaporate DCM and then centrifuged to collect solid microspheres. The resultant microspheres were washed with distilled water three times and freeze dried.

The microspheres were then compressed into disks and the bottoms and sides of the disks were sealed with a 35% w/v PCL/DCM solution (in a similar manner as described above for the pulsatile delivery device), leaving only the top unsealed. The device was dried in vacuum for 3 days.

The continuous delivery devices were formulated to have the identical shape, size, and component materials (i.e., drug (PTH), isolation/encapsulation material (polyanhydride copolymer), and sealant material (PCL)) as the pulsatile release devices. The continuous delivery device formed with BSA-containing microspheres was a control device.

In Vitro Testing

The BSA-containing pulsatile delivery devices (with SA:CPP:PEG=80:20:2 isolation layers with varying thicknesses of 50 µm, 100 µm and 200 µm), the PTH-containing pulsatile delivery device (with SA:CPP:PEG=80:20:2 isolation layers having a thickness of 50 µm), the BSA-containing continuous delivery devices (with different polyanhydride copolymer compositions), and the PTH-containing continuous delivery device (with different polyanhydride copolymer compositions) were used in in vitro testing.

The BSA-containing devices were immersed in 1 ml PBS (0.1 M, pH=7.4) and incubated at 37° C. After designated times, the medium was collected and replaced with equal amount of fresh PBS. The collected medium was stored at −80° C. until analysis. The amount of released BSA was measured using a MicroBCA protein assay (Pierce, Rockford, Ill.). In vitro bioactivity of released PTH (from the PTH-containing devices) was determined using the adenylate cyclase stimulation assay and cAMP-binding protein assay. For these tests, human fetal osteoblasts (hFOB) were treated with PTH of known concentrations or with eluent from the PTH delivery devices for designated times in calcium-free and magnesium-free hanks' balanced salt solution containing 0.1% BSA and 1 mM isobutylmethylxanthine (IBMX). After incubation of the treated cells at 37° C. for 10 minutes, the cAMP in the cells was extracted with ice cold perchloric acid. The cAMP extracts were then neutralized by adding KOH and centrifuged to remove the precipitates. ($^3$H)-cAMP was incubated with standards or unknowns and cAMP-binding protein for 90 minutes on ice. The unbound ($^3$H)-cAMP was removed by adding dextran-coated charcoal. The samples were then centrifuged and the supernatant of each tube was decanted to a scintillation tube. The radioactivity of the supernatants was determined using a liquid scintillation counter and cAMP levels were calculated using the standard curve.

Figure 12A:
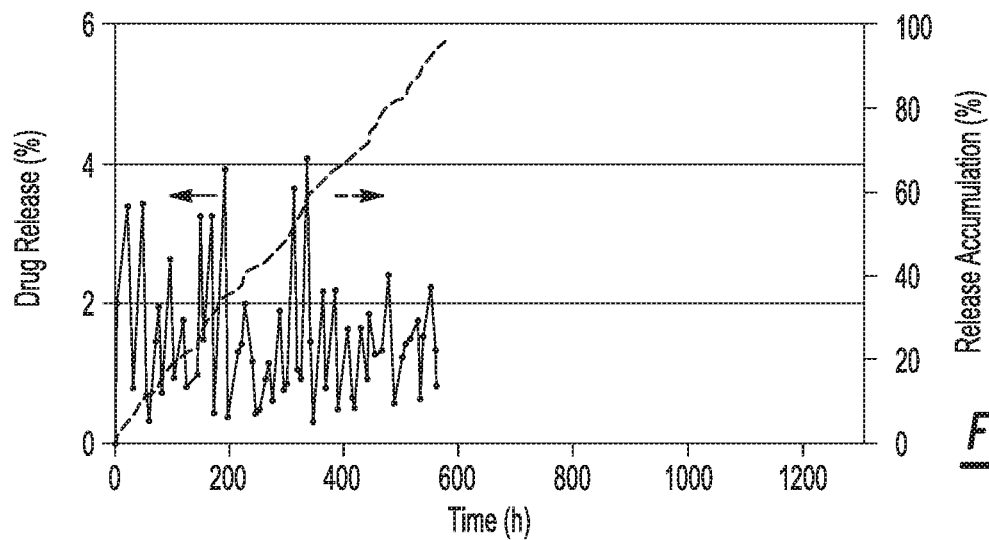
FIGS. 12A through 12C are graphs depicting the in vitro pulsatile Bovine serum albumin (BSA) release profiles from control pulsatile delivery devices with SA:CPP:PEG=80:20:2 isolation layers with varying thicknesses (12A, 50 μm; 12B, 100 μm; 12C, 200 μm)
Figure 12B:
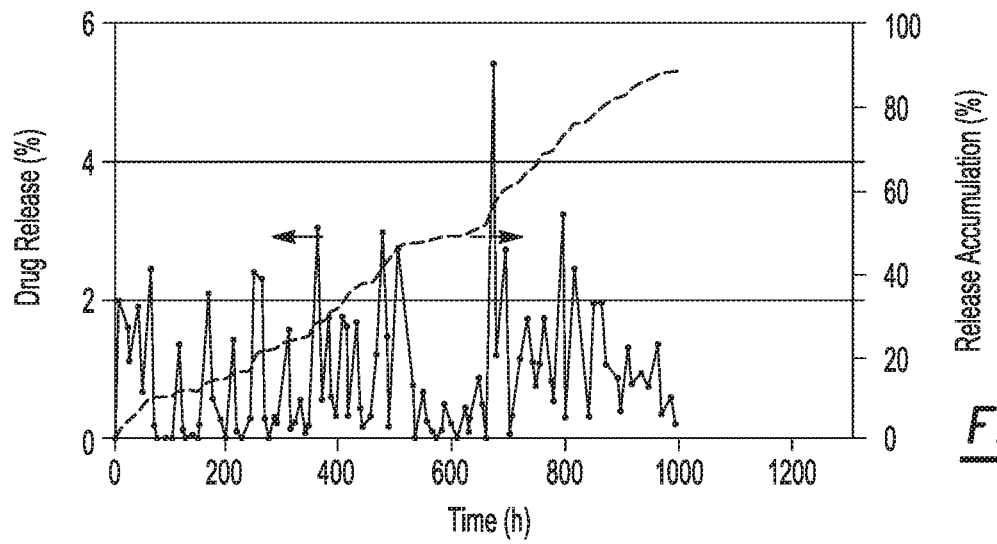
Figure 12C:
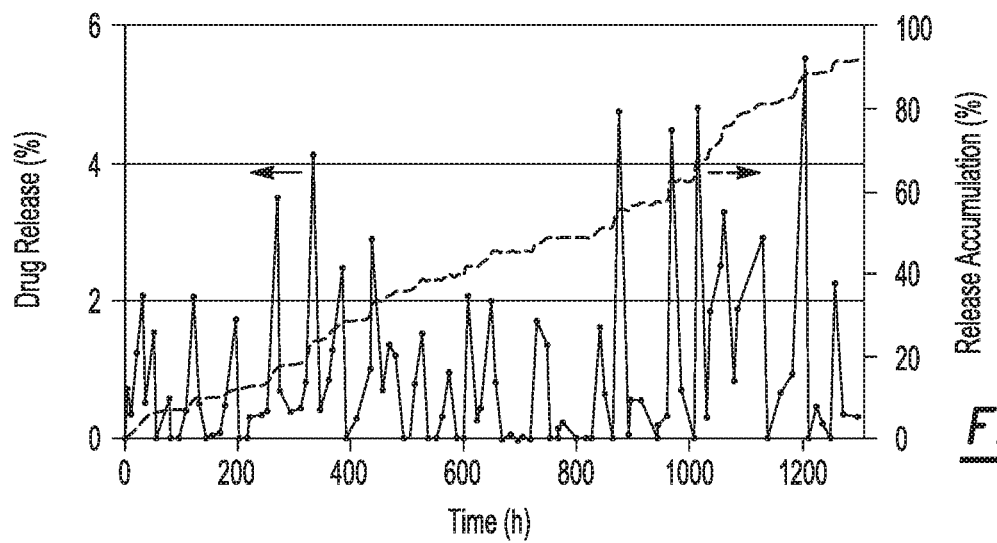
Figure 13:
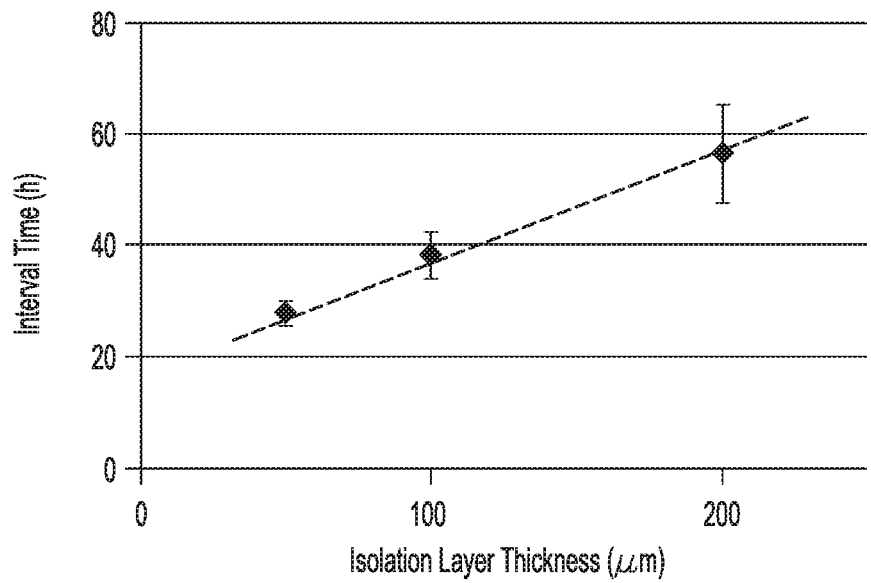
FIG. 13 is a graph illustrating that the average time interval (hours, h) between adjacent pulses exhibited a linear relationship with the thickness (μm) of the isolation layer.
Figure 14:
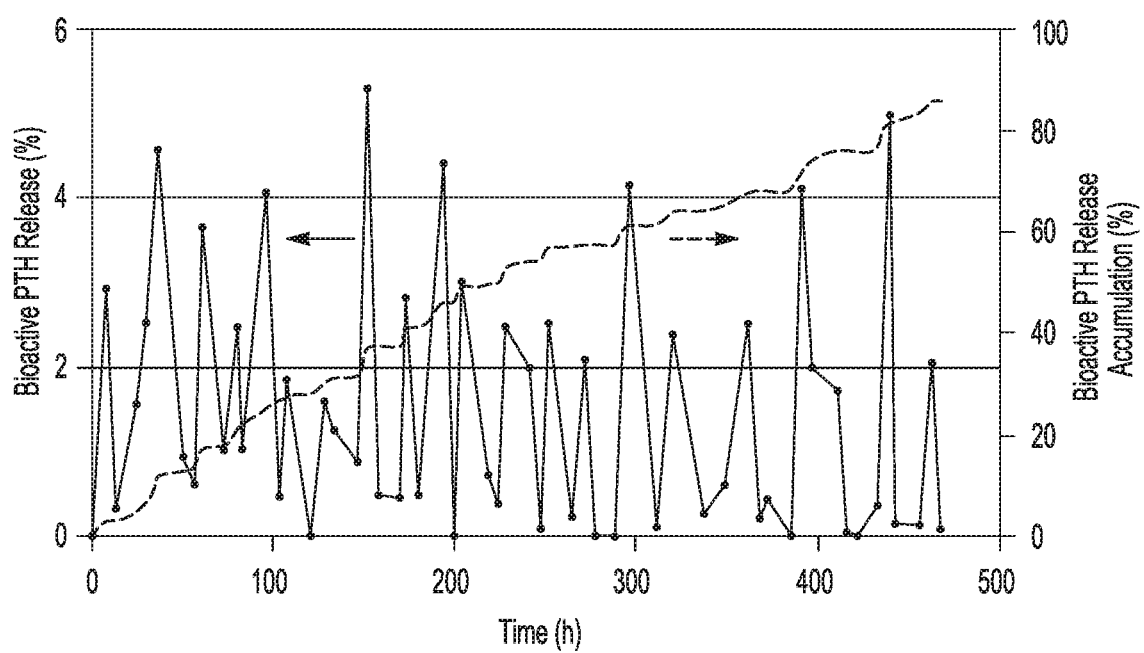
FIG. 14 is a graph depicting the in vitro pulsatile PTH release profiles from a pulsatile delivery device with 50 μm thick SA:CPP:PEG=80:20:2 isolation layers.

Each of the BSA-containing pulsatile delivery devices (with varying isolation layer thicknesses of 50 µm, 100 µm and 200 µm) were able to deliver 21 pulses of protein, just with different durations (see FIGS. 12A (50 µm thickness), 12B (100 µm thickness), and 12C (200 µm thickness)). As shown in FIG. 13, the average time interval between adjacent pulses for the BSA-containing pulsatile delivery devices exhibited a linear relation with the thickness of isolation layer. FIG. 14 depicts the results for the PTH-containing pulsatile delivery device (with 50 µm SA:CPP:PEG=80:20:2 isolation layers), which showed that 21 pulses of bioactive PTH were achieved over 3 weeks, and the released PTH retained around 80% bioactivity.

Figure 15:
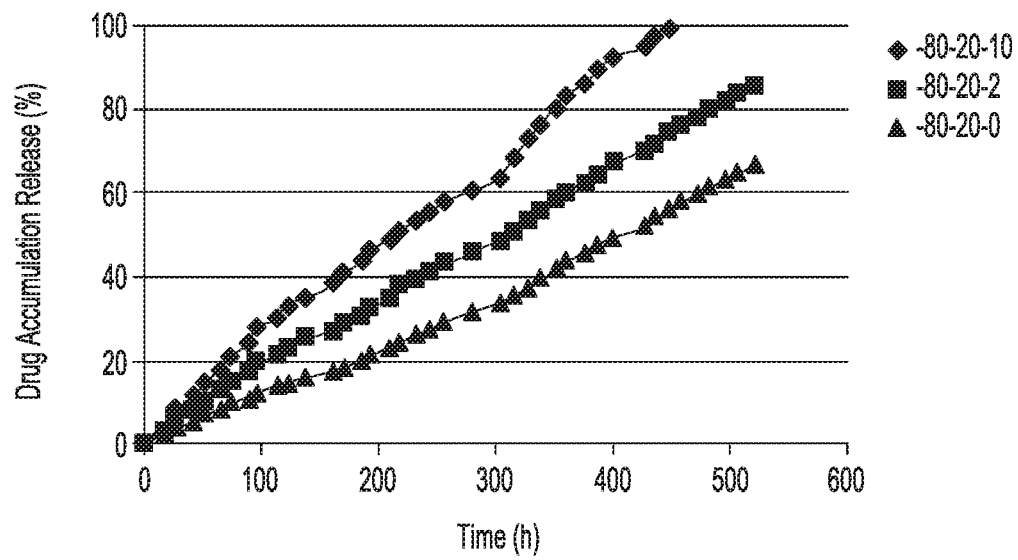
FIG. 15 is a graph depicting the in vitro continuous BSA release profiles from control continuous delivery devices with SA:CPP:PEG microspheres with varying compositions (80:20:0, 80:20:2, 80:20:10)

The BSA-containing continuous delivery devices achieved linear continuous release of the BSA, as shown in FIG. 15. Unlike most microsphere-based continuous delivery systems (such as poly(lactic-co-glycolic acid) (PLGA), polylactic acid (PLA), etc.), there was no burst release and the sustained release of BSA from the continuous release device disclosed herein was linear with the release time. The unidirectional device design may have contributed to the linear delivery kinetics, because the water can only erode spheres on the exposed disk surface and penetrate in the direction of the degrading surface. The results shown in FIG. 15 also illustrated that the drug release rate increased with increasing hydrophilic PEG segments in the three-component polyanhydride copolymer. The device made of the highest PEG content (~10%, i.e., 80:20:10) polyanhydride copolymer microspheres released all the drug in 400 hours, whereas the device made of the no PEG content (0%)

polyanhydride copolymer microspheres released 50% drug in 400 hours. The device with the 80:20:2 polyanhydride copolymer microspheres was able to release 90% of the drug (BSA) in 21 days, which was the targeted 3 weeks of anabolic window for PTH treatment.

Figure 16:
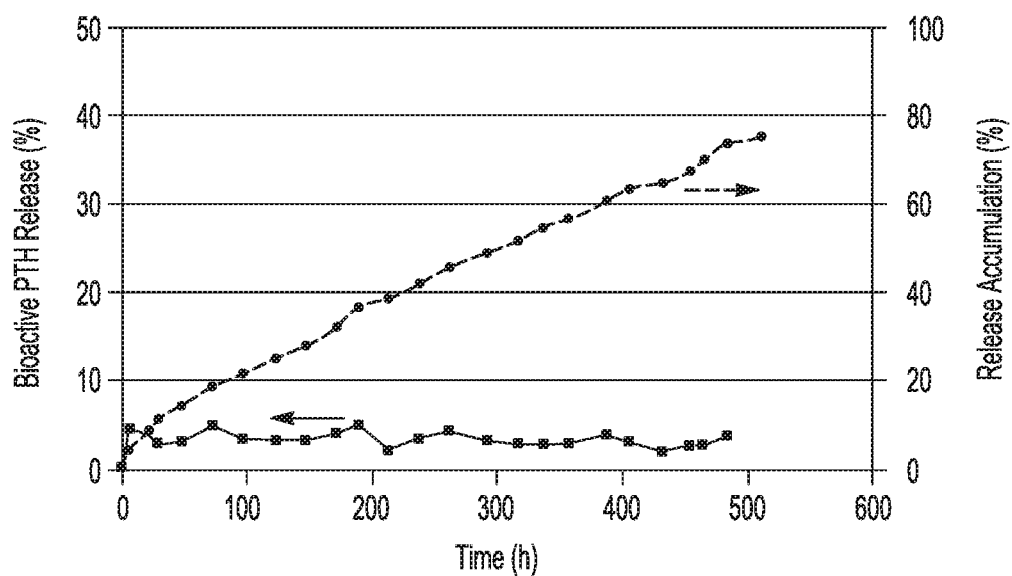
FIG. 16 is a graph depicting the in vitro continuous PTH release profiles from a continuous delivery device with SA:CPP:PEG=80:20:2 microspheres.

The PTH-containing continuous delivery device (with PTH-containing SA:CPP:PEG=80:20:2 polyanhydride copolymer microspheres) released PTH following a linear release profile (FIG. 16) with bioactivity not statistically different from that of released PTH from the pulsatile device (compare FIG. 16 with FIG. 14).

The continuous delivery device was formulated to have the identical shape, size, and component materials (i.e., drug (BSA or PTH), isolation/encapsulation material (polyanhydride copolymers), and sealant material (PCL)) as the pulsatile release device. As can be seen from the in vitro results, the PTH-containing continuous delivery device delivered the same total amount of PTH as the PTH-containing pulsatile release device, but in a continuous manner rather than an intermittent or pulsed manner. In the pulsatile device, PTH was isolated by the isolation layers in a layer-by-layer structure; whereas, in the continuous device, PTH was confined in micro-domains or nano-domains that were uniformly distributed throughout the individual microspheres, and thus throughout the device. The surface erosion property of the polymer used (in this example, the polyanhydride copolymer (SA-CPP-PEG)) to form the polymeric layers 12 in the pulsatile device and the microspheres 26 in the continuous device contributes to the two types of the release kinetics. In the pulsatile device, it enabled the daily-pulsed release because the water could only erode one isolation layer before releasing one drug layer. In the continuous device, the surface erosion property enabled the PTH release from microspheres on the exterior surface, and then gradually from those inside the device, resulting in the linear continuous drug release. Moreover, the structural tunability of the three-component polyanhydride copolymer enabled a broad range of interval time in the pulsatile device or release duration time in the continuous device.

In Vivo Testing

PTH has been shown to promote bone formation in vivo via a net anabolic action, but it inhibits osteoblast differentiation and mineralization in vitro, indicating that the in vivo environment cannot be replicated using in vitro model. Hence, an in vivo model is utilized to determine PTH's optimal delivery mode from the delivery devices.

The delivery devices utilized in the in vivo model included: the BSA-containing pulsatile delivery device (with SA:CPP:PEG=80:20:2 isolation layers having a thickness of 50 µm), the PTH-containing pulsatile delivery device (with SA:CPP:PEG=80:20:2 isolation layers having a thickness of 50 µm), the BSA-containing continuous delivery device (with SA:CPP:PEG=80:20:2 microspheres), and the PTH-containing continuous delivery device (with SA:CPP:PEG=80:20:2 microspheres).

In the in vivo model, the PTH action was evaluated in vivo to compare the pulsatile and continuous release modes in terms of anabolic effects on bone. The pulsatile and continuous devices—loaded with equal amounts of BSA or PTH—were implanted subcutaneously in mice (as described below). Three weeks later, the tibia, vertebrae and blood serum were collected and analyzed. MicroCT (µCT) scanning showed that PTH released from the devices had obvious effects on the tibias.

All animal procedures were carried out under the guidelines of, and were approved by the Institutional Animal Care and Use Committee of the University of Michigan. Pulsatile or continuous BSA or PTH delivery devices were implanted into subcutaneous pockets created from a midline incision on the backs of C57B6 mice (The Jackson Laboratory, Bar Harbor, Me.) at postnatal day 10. Three weeks after implantation, the mice were euthanized and whole blood was obtained by intracardiac blood draw. Serum was separated and kept frozen until biochemical assays were performed. The serum TRAP5b and P1NP immunoassays were performed per manufacturer's protocols. Three dimensional analyses of mice tibiae were performed using µCT. Briefly, formalin fixed tibiae were embedded in 1% agarose and placed in a 19 mm diameter tube and scanned over their entire length using a µCT system (µCT100 Scanco Medical, Bassersdorf, Switzerland). The scan settings were: 12 µm voxel size, medium resolution, 70 kVp, 114 µA, 0.5 mm AL filter, and an integration time of 500 ms. Trabecular bone parameters were measured over 50 slices using an 180 mg/cm$^3$ hydroxyappetite (HA) threshold beginning 15 slices distal to the growth plate; cortical bone parameters were measured over 30 slices beginning 250 slices proximal to the tibia-fibular joint (TFJ) using a 280 mg/cm$^3$ HA threshold. The trabecular bone volume (BV/TV) and cortical bone thickness (Ct.Th) were quantified using the manufacturer's evaluation software (Scanco µCT 100).

Mice vertebrae were also harvested for histological analyses. Histomorphometric analyses were performed. After fixation and decalcification, paraffin-embedded tibiae and vertebrae were cut (5 µm), stained with hematoxylin and eosin, and bone areas were measured using a computer-assisted histomorphometric analyzing system (Image-Pro Plus version 4.0; Media Cybernetics, Inc., Silver Spring, Md.). TRAP staining was performed using the Leukocyte Acid Phosphatase Assay (Sigma) following the manufacturer's protocol.

For the in vivo results, all P values were calculated by an unpaired, two-tailed t test using GraphPad InStat software (GraphPad). All data are means±SD.

Figure 17:
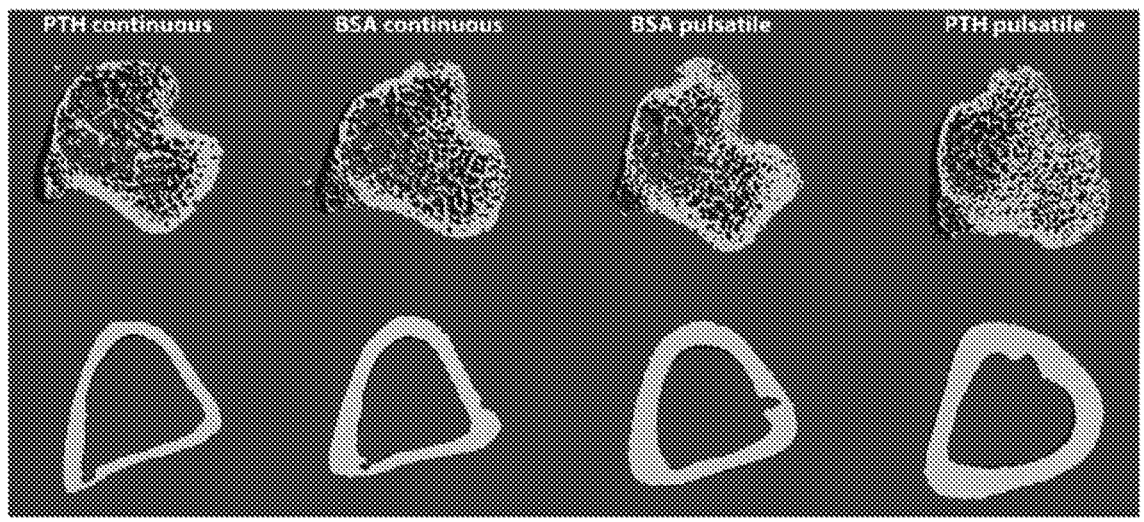
FIG. 17 illustrates, in black and white, the representative μCT reconstruction of trabecular bone (top images) and cortical bone (bottom images) of mouse tibias treated with a BSA-containing pulsatile delivery device (with SA:CPP:PEG=80:20:2 isolation layers having a thickness of 50 μm), a PTH-containing pulsatile delivery device (with SA:CPP:PEG=80:20:2 isolation layers having a thickness of 50 μm), a BSA-containing continuous delivery device (with SA:CPP:PEG=80:20:2 microspheres), and a PTH-containing continuous delivery device (with SA:CPP:PEG=80:20:2 microspheres)
Figure 18A:
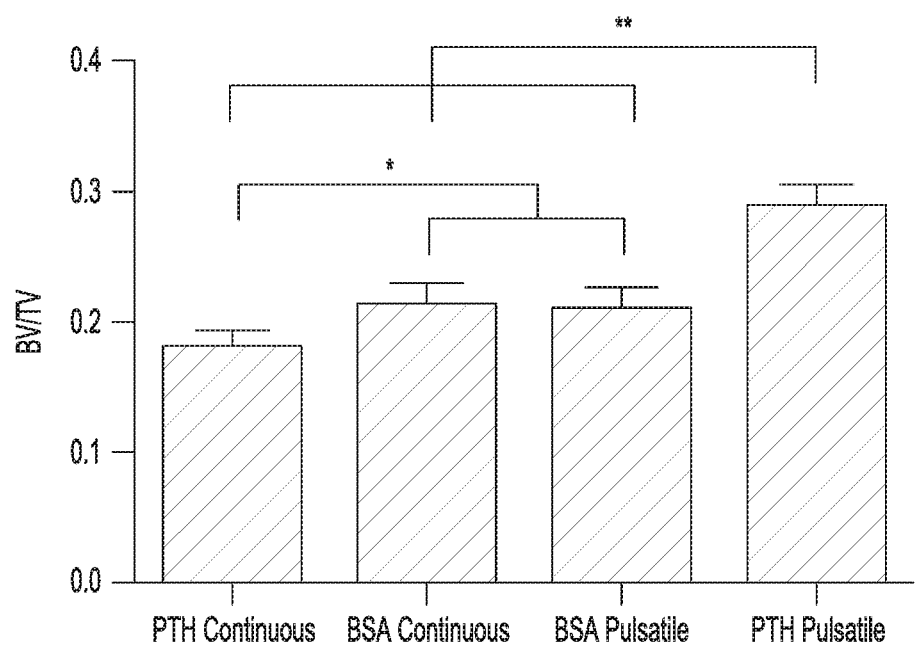
FIGS. 18A and 18B are graphs respectively depicting the trabecular bone volumes (bone volume/total volume, BV/TV) and cortical bone thicknesses (Ct. Th) (mm) of the mouse tibias treated with the BSA-containing pulsatile delivery device (with SA:CPP:PEG=80:20:2 isolation layers having a thickness of 50 μm), the PTH-containing pulsatile delivery device (with SA:CPP:PEG=80:20:2 isolation layers having a thickness of 50 μm), the BSA-containing continuous delivery device (with SA:CPP:PEG=80:20:2 microspheres), and the PTH-containing continuous delivery device (with SA:CPP:PEG=80:20:2 microspheres) (n=5-7 per group, $P^*<0.05$, $^{**}P<0.005$)
Figure 18B:
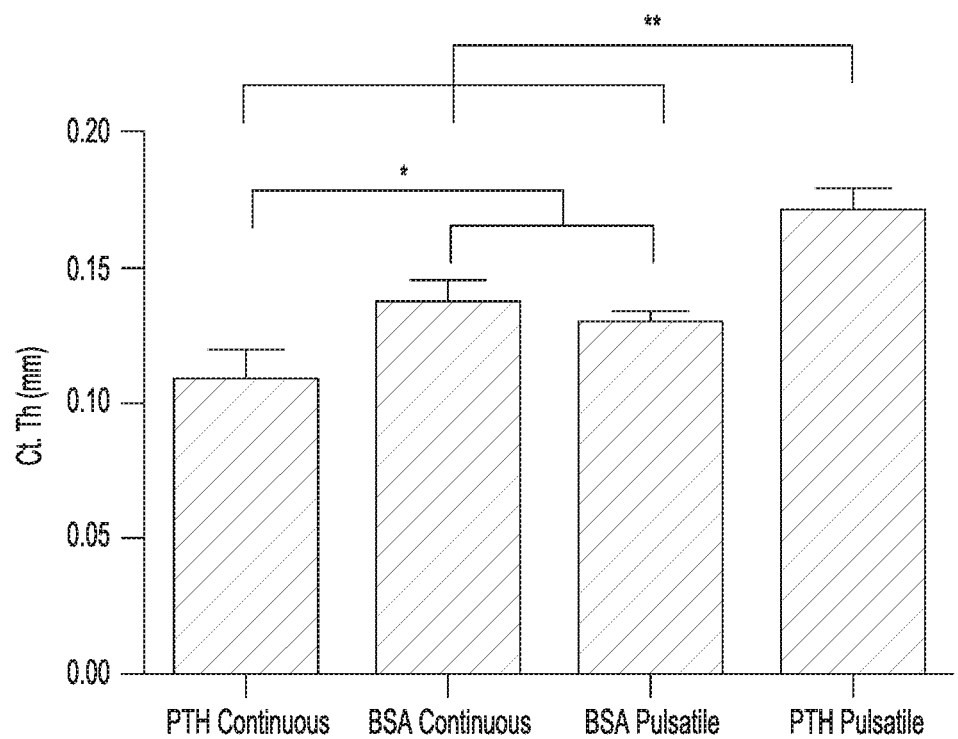

FIG. 17 illustrates the representative µCT reconstruction of trabecular bone (top images) and cortical bone (bottom images) of the mouse tibias from the groups treated with the different delivery devices. FIGS. 18A and 18B are graphs respectively depicting the trabecular bone volumes and the cortical bone thickness. The 3D reconstruction (FIG. 17) and the quantitative analysis (FIGS. 18A and 18B) showed that the pulsatile PTH release significantly increased trabecular bone volume and cortical bone thickness, while the continuous PTH release acted in the opposite way and decreased both trabecular bone volume and cortical bone thickness.

Figure 19A:
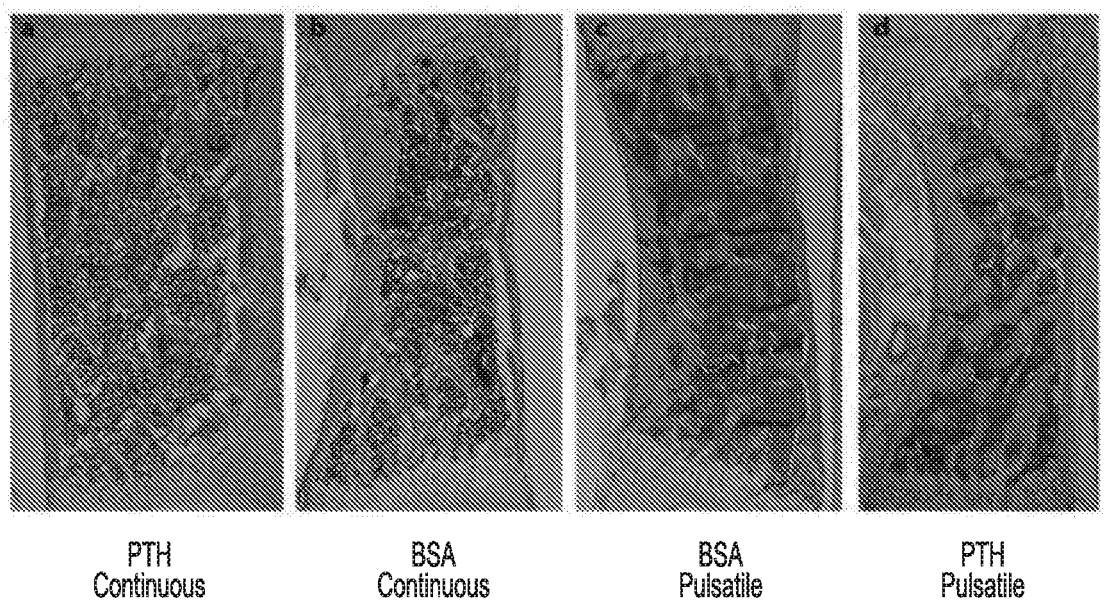
FIGS. 19A, 19B, and 19C respectively depict (19A) black and white images representative of H&E staining of vertebrae treated with the different delivery devices, (19B) vertebral bone area/tissue area (BA/TA) analyzed by histomorphometry, and (19C) serum P1NP level (pg/ml) measured by P1NP ELISA (pulsatile groups: n=9~12/group, continuous groups: n=6~9/group, $^*P<0.05$, $^{**}P<0.005$)
Figure 19B:
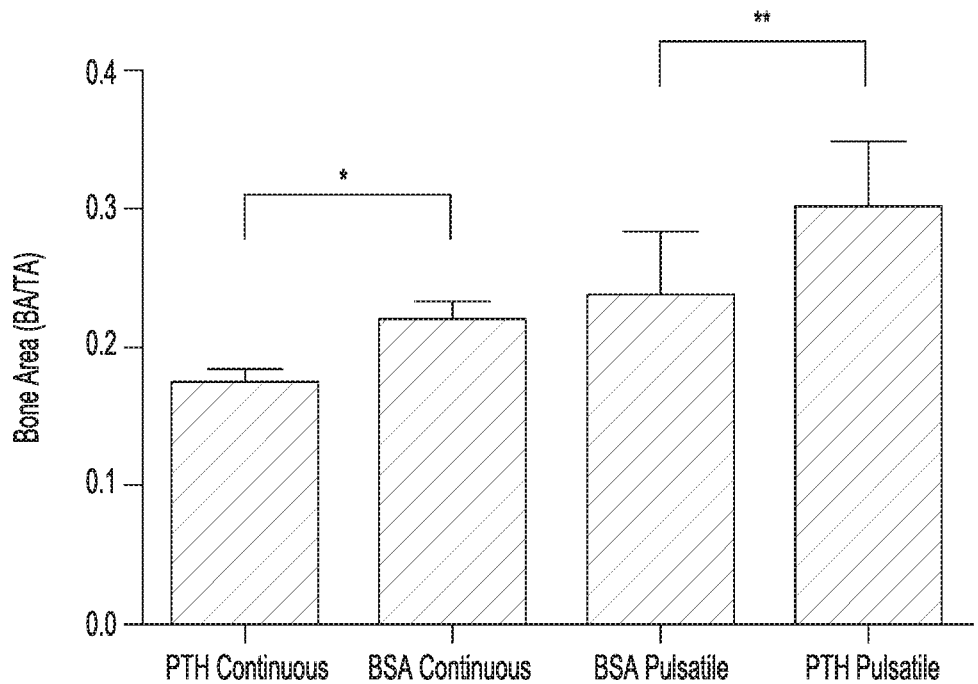
Figure 19C:
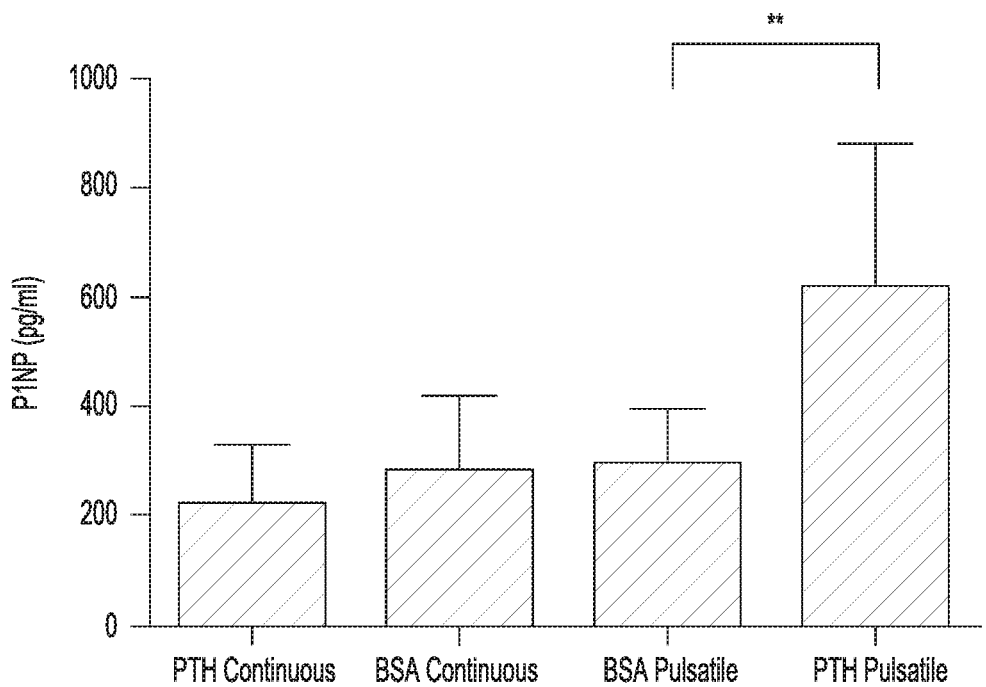
Figure 20A:
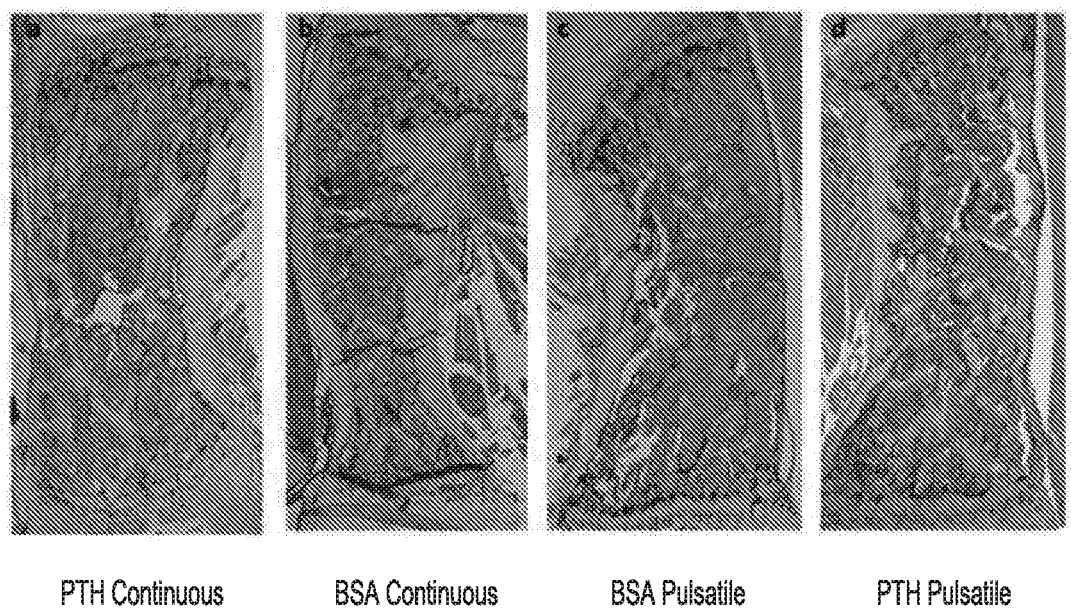
FIGS. 20A, 20B, and 20C respectively depict (20A) black and white images representative of TRAP staining of vertebrae treated with the different delivery devices, (20B) osteoclast numbers per bone perimeter (OSC #/mm bone), and (20C) serum TRAP5b level (units per liter, U/L) measured by ELISA (pulsatile groups: n=9~12/group, continuous groups: n=6~9/group, $^*P<0.05$, $^{**}P<0.005$)

The vertebral bone turnover and the osteoclastic response to the systemic PTH releases were examined using hematoxylin and eosin (H&E) staining (FIG. 19A, shown in black and white) and tartrate-resistant acid phosphatase (TRAP) staining (FIG. 20A, shown in black and white). Quantitative analysis of the bone area ratio showed that pulsatile PTH significantly increased bone area, while continuous PTH significantly decreased bone area compared to the respective BSA control devices (FIG. 19B). The serum bone formation marker (procollagen I intact N-terminal propeptide (PINP)) level was measured using an enzyme-linked immunosorbent assay (ELISA) and showed that the PINP levels were significantly elevated in the pulsatile PTH group (FIG. 19C).

Figure 20B:
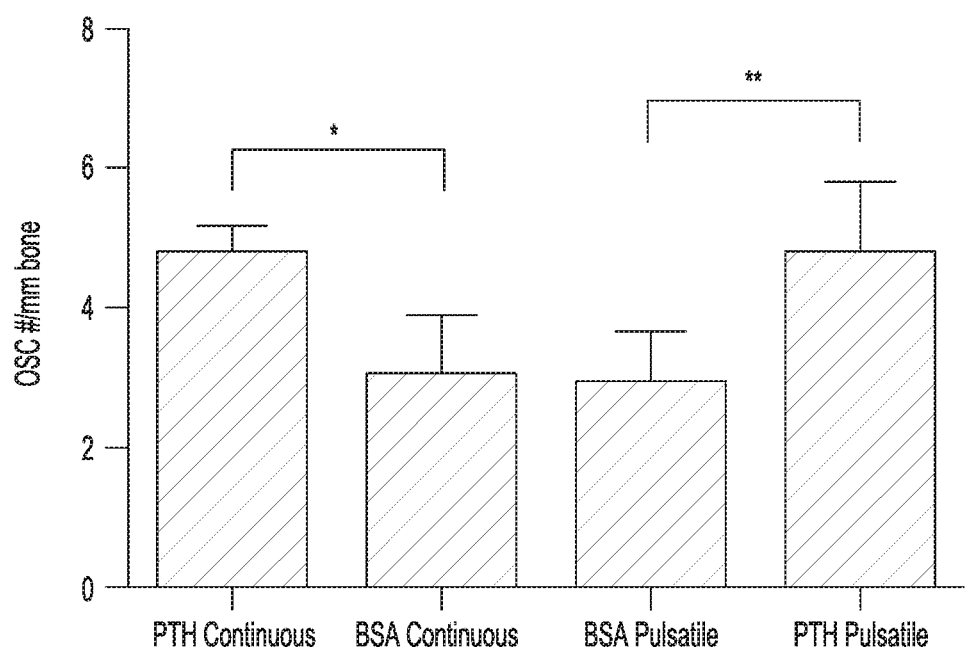
Figure 20C:
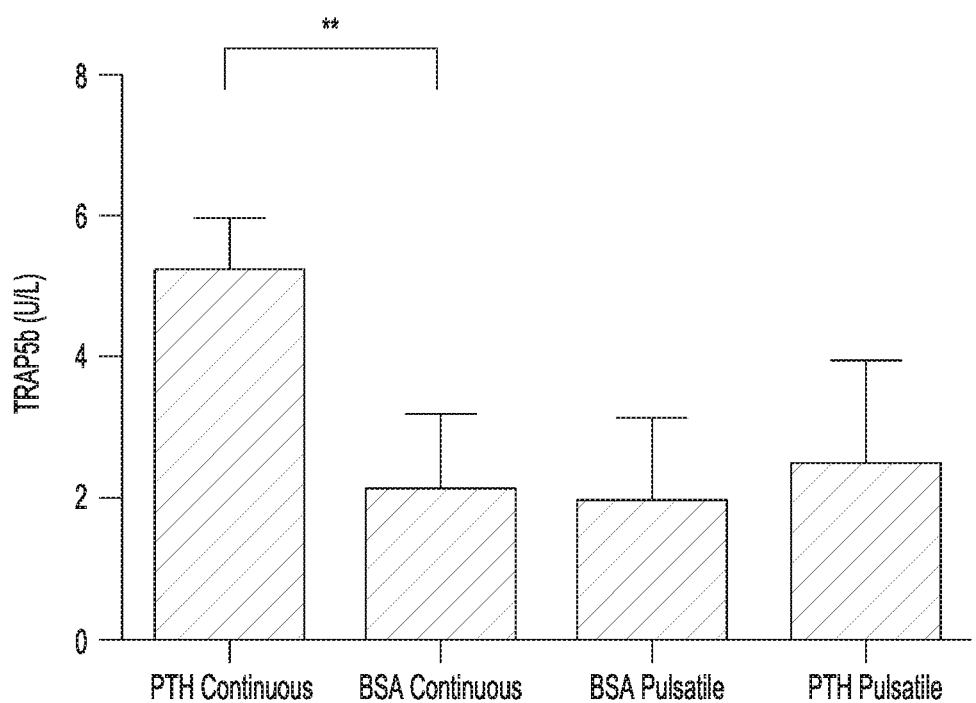

Interestingly, TRAP staining of the vertebrae showed that both PTH pulsatile and continuous delivery led to an increased number of TRAP-positive osteoclasts per bone perimeter (FIG. 20A, shown in black and white, and FIG. 20B showing the quantitative results), but the serum bone resorption marker TRAP 5b level was significantly higher only for continuous PTH release (FIG. 20C).

These in vivo results indicated that while delivering the same amount of PTH, the pulsatile release device enhanced bone growth through increasing bone remodeling (as evidenced by an increase in bone formation marker P1NP and enhanced osteoclast numbers), while continuous release induced bone resorption through the enhanced osteoclast activity. The systemic pulsatile PTH release was found to be superior in terms of anabolic action in bone.

Figure 21:
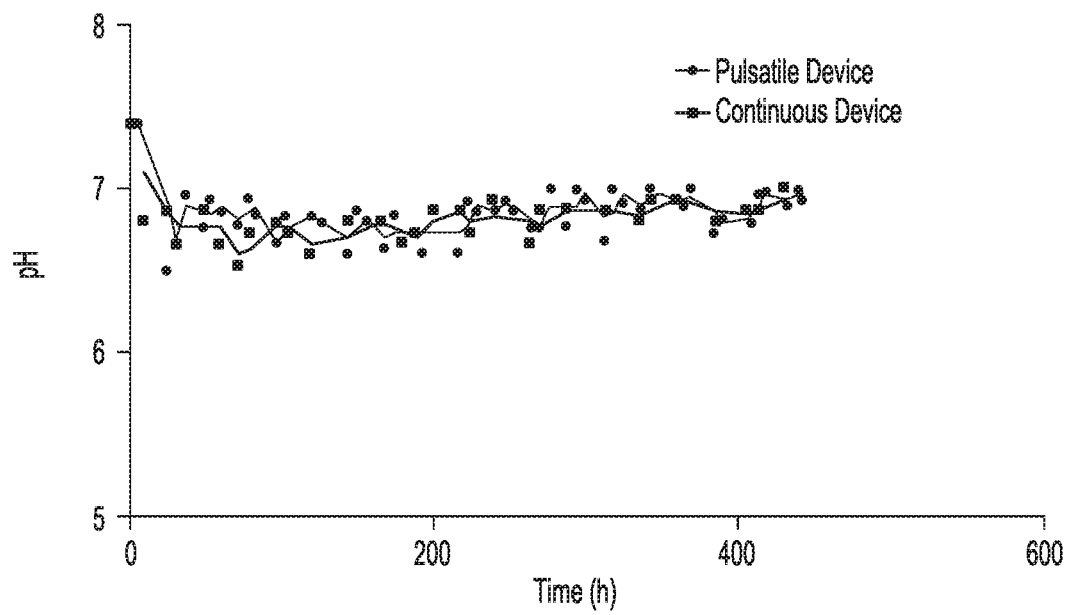
FIG. 21 is a graph depicting the change of solution pH value over time when the delivery devices were immersed in 1 ml 0.1M PBS at 37° C.
Figure 22:
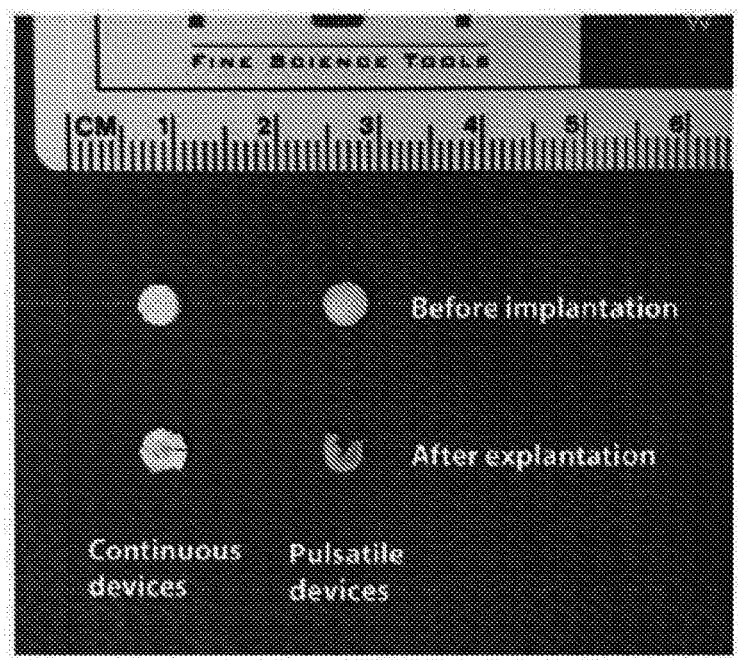
FIG. 22 is a picture of the PTH drug delivery devices of Example 1 before implantation and after 3-week implantation.
Figure 23A:
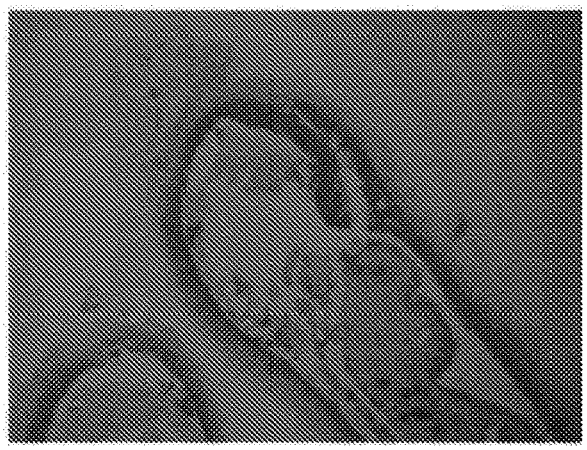
FIGS. 23A through 23D depict black and white images of H&E staining of the PTH pulsatile delivery device at 2× (23A), 20× (23B), and of the PTH continuous delivery device at 2× (23C) and 20× (23D)
Figure 23B:
Figure 23C:
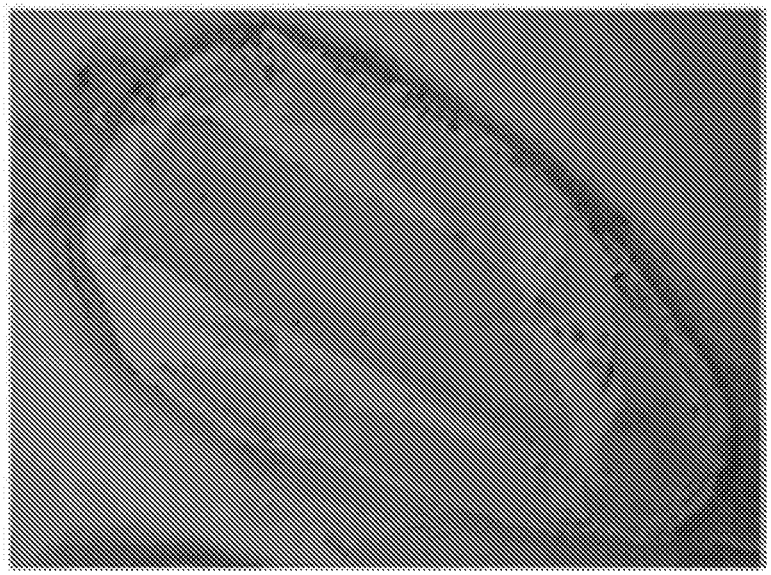
Figure 23D:
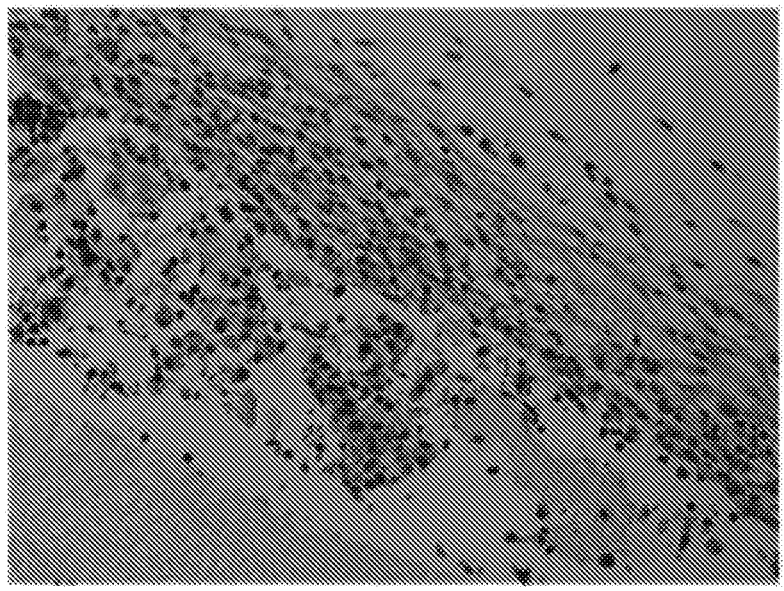

To investigate the biocompatibility, the pH value change during the degradation of the devices in vitro was measured, and the body response to the implants in vivo was also measured. The pH value of the PBS medium, in which devices were immersed, remained about 6.8, close to neutral pH 7, over time as the devices degraded. There was no significant difference between pulsatile and continuous devices (FIG. 21) since the same amounts of polyanhydride copolymer were used to fabricate the two types of devices. The in vivo body response to the devices was evaluated using histological analysis of the devices explanted 3 weeks after subcutaneous implantation. Most parts of the devices had been degraded, leaving the slow degrading sealant shell of PCL (FIG. 22), which would degrade eventually. H&E staining was performed to assess inflammation at the implant sites in vivo (FIGS. 23A-23D, shown in black and white). The devices were mainly surrounded by granulation tissue composed mostly of macrophages and lymphocytes and partial encapsulation by a fibrovascular connective tissue wall was noted. The inflammatory infiltrate was localized to the area surrounding the devices with limited extension into the adjacent adipose tissue. These results indicate that overall, all the materials (alginate, PA and PCL) used to construct the delivery devices are biocompatible and biodegradable. Subcutaneous implanted devices degraded in vivo and resulted in an encapsulation of the materials with minimal acute inflammation.

Conclusion

The pulsatile device was preprogrammed to deliver daily pulse of bioactive PTH and the continuous device to deliver bioactive PTH in a linear manner for 3 weeks. The results in Example 1 demonstrate that the systemic pulsatile PTH release was able to increase bone via enhancing bone remodeling, whereas the continuous PTH release resulted in bone resorption via elevated osteoclast resorption activity. The biodegradable pulsatile PTH delivery device has the potential to be a patient friendly PTH therapy, which could be administered only once (implantation) instead of daily injection. In addition, the devices are biodegradable and resorbable in vivo, eliminating the need of removal surgery.

Beyond the PTH delivery application, the platforms (continuous and pulsatile devices) may be useful in fundamental and translational studies on how temporal effects and release patterns of biomolecules regulate cell fate, tissue development and regeneration.

Example 2

This example was performed to examine the ability of the PTH delivery devices to spatially control local bone defect regeneration. The experimental design is shown in FIG. 24. A three-dimensional (3D) cell-free scaffold (support structure 32) was implanted in a mouse calvarial defect with either the pulsatile delivery device 10 or the continuous delivery device 10'. Serum was collected three weeks later to examine the systemic effects of the PTH release modes on bone. Bones were collected eight weeks later to examine the effects of the PTH release mode on bone regeneration.

In Example 2, all numerical data are presented as mean±SD. All P values were calculated by an unpaired, two-tailed t test using GraphPad InStat software (GraphPad). P<0.05 was considered statistically significant.

Nanofibrous Scaffold

Poly(L-lactic acid) (PLLA, Resomer L207S) with an inherent viscosity of 0.8~1.2 dl/g was purchased from Boehringer Ingelheim (Ingelheim, Germany).

Figures 25A, 25B, 25C:
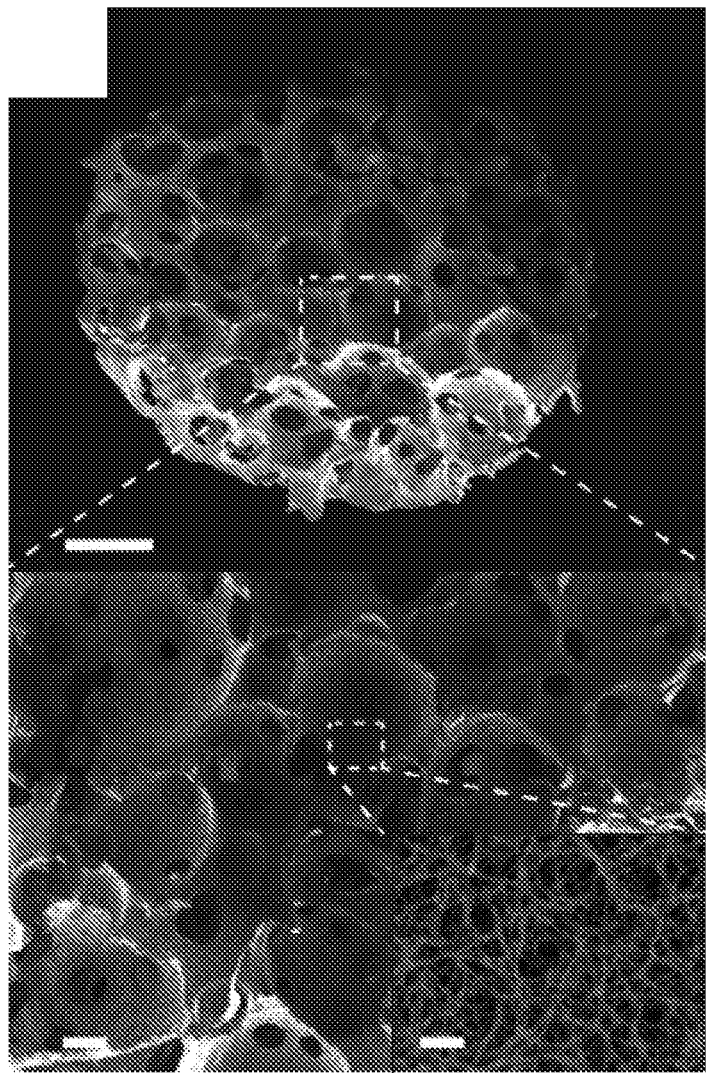
FIGS. 25A through 25C are SEM images of a nanofibrous scaffold with an interconnected spherical pore network, where the scale bar is 400 μm in FIG. 25A, 50 μm in FIG. 25B, and 2 μm in FIG. 25C.

3D nanofibrous PLLA scaffolds with inter-connected spherical pores were fabricated using a combination of sugar leaching and thermally induced phase separation. Fructose sugar spheres were made and sifted with standard sieves to separate them by size. Spheres of the desired size were collected, added to a mold, and heat-treated to achieve the desired interconnected pore structure. A PLLA/tetrahydrofuran (THF) (10% w/v) solution was then cast onto the sugar sphere assembly and the whole construct was stored at −80° C. over night to induce phase separation. The phase-separated samples were immersed into distilled water to extract the solvent and leach away the sugar spheres. The PLLA scaffolds were freeze-dried and punched into a desired size. SEM images of the scaffold are shown in FIGS. 25A through 25C. FIG. 25A shows the complete scaffold (scale bar is 400 µm) and FIGS. 25B and 25C illustrate the nanofibrous architecture of the scaffold (i.e., the images were taken at higher magnifications, and the scale bar in FIG. 25B is 50 µm, while the scale bar in FIG. 25C is 2 µm). The spherical pores of the scaffold ranged from 250 µm to 420 µm and the porosity was as high as 98.5%. The surface of the scaffold mimicked the nanfibrous feature of type I collagen matrices (the main organic extracellular matrix component of bone).

Pulsatile Delivery Device

Multi-pulse BSA and PTH delivery devices were formulated. The devices were made of alternating drug layers (substance layers 14) and isolation layers (polymeric layers 12), and was formed via the method shown in FIG. 1.

The isolation layers were made of three-component polyanhydride copolymers (PA copolymer), which are biocompatible, and biodegradable through surface erosion. The PA copolymer was composed of anhydrides of sebacic acid (SA), 1,3-bis (p-carboxyphenoxy) propane (CPP), and poly (ethylene glycol) (PEG, Mw=1000), and was formed by condensation polymerization. The PEG segments were incorporated into the copolymer to increase the hydrophilicity and improve the hydrolytic degradation. The composition of the three-component polyanhydride copolymer was 80 SA:20 CPP:2 PEG. The three-component polyanhydride copolymer was melted and hot compressed into layers of 50 µm thickness with error ±5 µm. The PA copolymer layers were punched into disks of desired size (3 mm in diameter) to form the isolation layers.

BSA or PTH (1-34) (Bachem Bioscience Inc., Torrance, Calif.) was mixed with alginate in a 1:1.67 weight ratio to form the drug layers. Alginate was used as the drug/protein carrier because of its biocompatibility and processability. The mixture was dissolved in distilled water and the solution was cast into a film and freeze-dried for 1 day. The alginate-BSA and alginate-PTH films were then punched into disks of desired size (1.5 mm in diameter) to form the drug layers.

The drug layers were designed to be smaller than the isolation layers to prevent possible contact between adjacent drug layers, which could lead to the leakage of drug between layers.

The isolation layers were rubbed with a TEFLON® film to generate positive surface charges and the drug layers (containing PTH or BSA) were rubbed with a glass slide to generate negative surface charges. The electrostatic voltages of the two different layers were measured using a non-contact static meter (Electro-Tech Systems Static Meter Model 200). The results indicated that opposite charges were generated on the isolation layer (i.e., polyanhydride film) (about +157 mV ±67 mV) and the drug layer (alginate-PTH film) (about −80 mV ±30 mV).

To calculate the PTH loading efficiency, PTH-loaded devices were hydrolyzed by a mixture of 0.5 ml of 1MNaOH and 0.5 ml PBS with shaking at room temperature for 2 hours. After hydrolysis, 0.5 ml of 1 M HCl was added to neutralize the sample solutions. The samples were centrifuged at 3000 rpm for 5 minutes and the supernatant samples were collected. Protein amounts in the supernatant were determined by MicroBCA method (Pierce, Rockford, Ill.). The loading efficiency was determined by dividing the retained PTH amount over initially loaded PTH amount. The PTH loading efficiency of the pulsatile device was as high as 98.5%.

One charged isolation layer and one charged drug layer (PTH for one device and BSA for a control device) were placed into contact. The oppositely charged layers were attracted to each other to form one bi-layer structure. 21 bi-layer structures were stacked up, and the two outermost layers of the stack were an isolation layer at one end and a drug layer at the other end. A clamp was used to compress the multilayer structure/stack from the top and the bottom to ensure the close contact between layers. PCL was dissolved in DCM to form a 35% w/v viscous clean solution, and 50 µl of the PCL/DMC solution was carefully casted and coated onto the cylindrical side and on the outermost drug layer to form a construct. The outermost isolation layer was left exposed or unsealed, which ensured one-direction erosion (e.g., from the outermost isolation layer to the drug layer in direct contact with the PCL sealant layer) and thus unilateral drug release from the formed device. The construct was subject to vacuum (10 in Hg) for about 1 minute to allow the PCL to penetrate and seal the gaps between the isolation layers (which were created due to the difference in diameter between the isolation and drug layers). The sealing process was repeated 3 times and then the whole device was dried under vacuum (20 in Hg) for 3 days. The sealing technique enabled close contact between drug layers and isolation layers and eliminated air gaps.

Figure 26A:
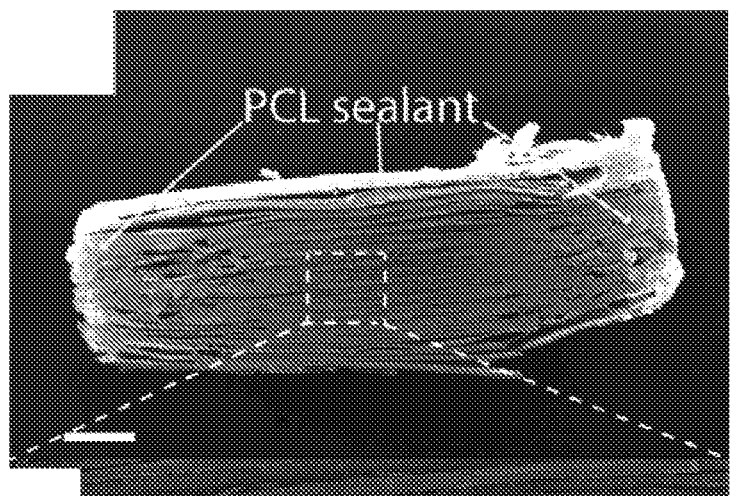
FIGS. 26A and 26B are SEM images of a PTH pulsatile delivery device of Example 2, where the scale bar is 400 μm in FIG. 26A and 50 μm in FIG. 26B.
Figure 26B:
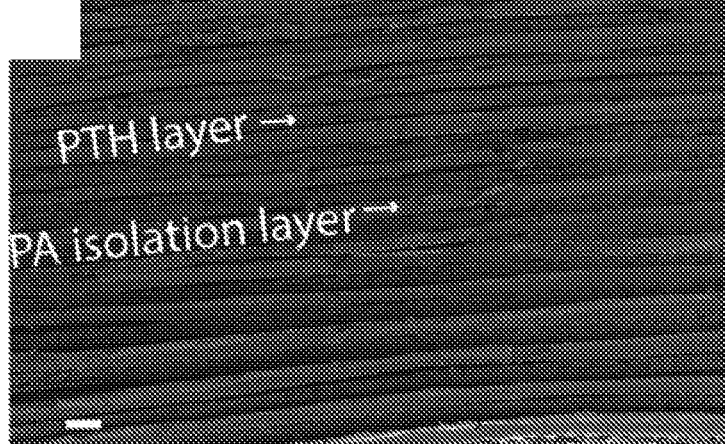

SEM images of the PTH pulsatile delivery device are shown in FIGS. 26A and 26B. FIG. 26A shows the complete device (scale bar is 400 µm) and FIG. 26B illustrates the layer-by-layer configuration of a portion of the pulsatile delivery device (i.e., the images were taken at a higher magnification, and the scale bar in FIG. 26B is 50 µm).

The pulsatile delivery device formed with BSA was a control device.

Continuous Delivery Device

PTH continuous delivery devices were formulated. The continuous delivery devices were made of PTH-encapsulated polyanhydride copolymer microspheres, and were formed via the double emulsion method shown in FIG. 2.

To form the PTH-encapsulated polyanhydride copolymer microspheres, PTH was first dissolved in distilled water with 0.1% w/v BSA/gelatin (the combination of which was used to prevent denaturation during the double emulsion) to form a drug solution. 200 µl of the drug solution was emulsified into 1 ml of a 10% w/v polyanhydride copolymer/dichloromethane (DCM) solution, using a probe sonicator at an output power of 10 W (Virsonic 100, Cardiner, N.Y.), for 20 seconds over an ice bath to form the water-in-oil (w/o) emulsion. The polyanhydride copolymer was formed with a monomer feed ratio of 80 SA:20 CPP:2 PEG. The w/o emulsion was then gradually added into 20 ml of an aqueous polyvinyl alcohol (PVA) solution (1% w/v) under sonication at an output power of 20 W to form a water-in-oil-in-water (w/o/w) double emulsion. The double emulsion was stirred at room temperature for 3 hours to evaporate DCM and then centrifuged at 6000 rpm for 6 minutes to collect solid microspheres. The resultant microspheres were washed with distilled water three times and freeze dried.

The PTH-encapsulated microspheres (having a size ranging from about 1 µm to about 20 µm) were then compressed into disks and the bottoms and sides of the disks were sealed with a 35% w/v PCL/DCM solution (in the same manner as described above for the pulsatile delivery device), leaving only the top unsealed. The device was dried in vacuum for 3 days.

The continuous delivery devices were formulated to have the identical shape, size, and component materials (i.e., drug (PTH), isolation/encapsulation material (80 SA:20 CPP:2 PEG polyanhydride copolymer), and sealant material (PCL)) as the PTH pulsatile release devices. The difference between the pulsatile and continuous types of devices is the PTH distribution, where PTH is distributed in a layered structure to achieve pulsatile release or PTH is more uniformly distributed in the matrix within microspheres to achieve continuous release.

To calculate the PTH encapsulation efficiency, 5 mg PTH-loaded PA microspheres were hydrolyzed to measure the amount of the protein encapsulated, using the same procedure as the pulsatile device. The encapsulation efficiency was determined by dividing the retained PTH amount over the initially loaded PTH amount. The microspheres encapsulation efficiency was calculated to be 86.3±3.2%.

SEM images of the PTH continuous delivery device are shown in FIGS. 27A and 27B. FIG. 27A shows the complete device (scale bar is 400 µm) and FIG. 27B illustrates the PTH-loaded microspheres in a portion of the continuous delivery device (i.e., the images were taken at a higher magnification, and the scale bar in FIG. 27B is 50 µm).

In Vitro Testing

The PTH pulsatile and continuous delivery devices were immersed in 1 ml PBS (0.1 M, pH=7.4) and incubated at 37° C. The medium was collected at designated time points and replaced with equal amount of fresh PBS. The samples were stored at −80° C. until analysis. The amount of released PTH was measured using PTH ELISA kit (Immutopics, Inc). The bioactivity of released PTH was determined using the adenylate cyclase stimulation assay and cAMP-binding protein assay.

Figure 29:
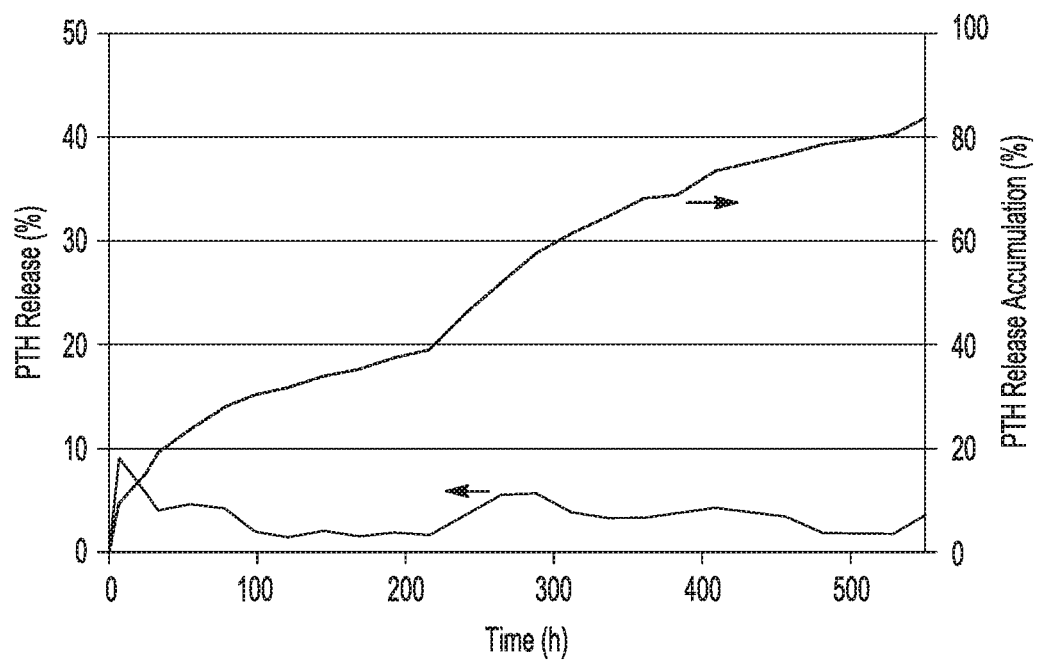
FIG. 29 is a graph depicting the in vitro continuous PTH release profiles from the continuous delivery device of Example 2 with SA:CPP:PEG=80:20:2 microspheres.

As shown in Example 1, for the pulsatile delivery device, the interval time between two adjacent PTH peaks exhibited a linear relationship with the thickness of isolation layer (see FIG. 13). In this Example, the device with twenty-one SA:CPP:PEG=80:20:2 isolation layers with a thickness of 50 µm was able to achieve the desired 21 daily pulses of release. The ELISA data, shown in FIG. 28, illustrates that the pulsatile release device released around 90% of the PTH in a pulsatile manner over the 21 days. The same SA:CPP:PEG=80:20:2 polyanhydride copolymer was used in the form of microspheres to achieve continuous drug release for 21 days from the continuous release device. FIG. 29 illustrates the ELISA data for the continuous release device. As illustrated, nearly the same amount of PTH was released in a linear manner for 21 days. In both FIGS. 28 and 29, the relatively linear curves were the cumulative PTH release curves measured using the PTH ELISA kit.

Figure 30A:
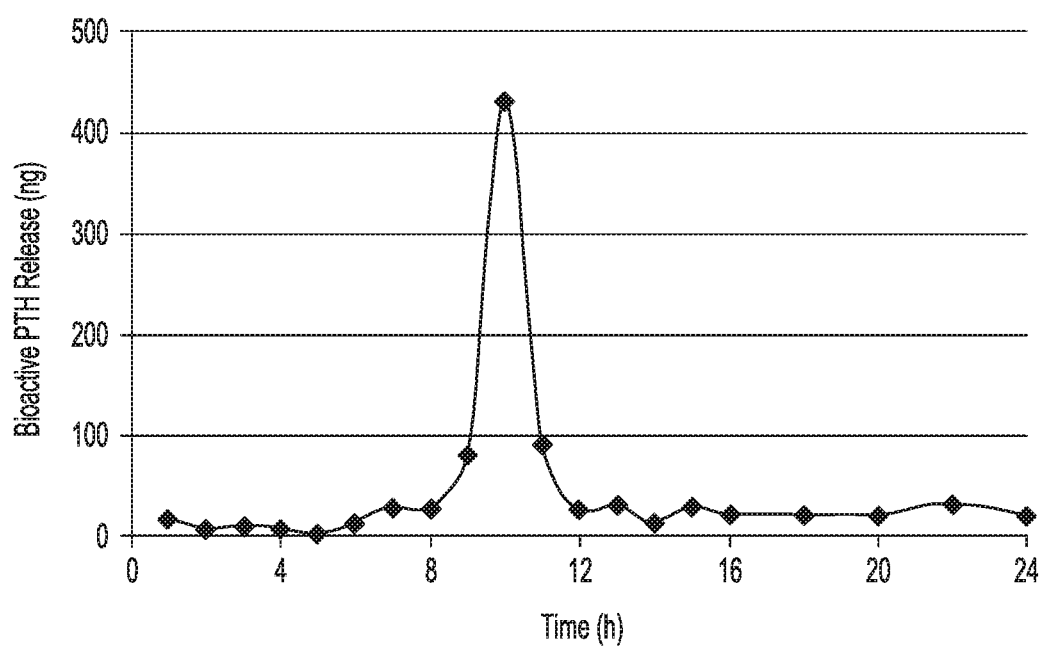
FIGS. 30A through 30C are graphs graph depicting the in vitro bioactive PTH release curves (ng versus hours) from the pulsatile delivery device of Example 2 on day 1, day 10, and day 20, respectively.
Figure 30B:
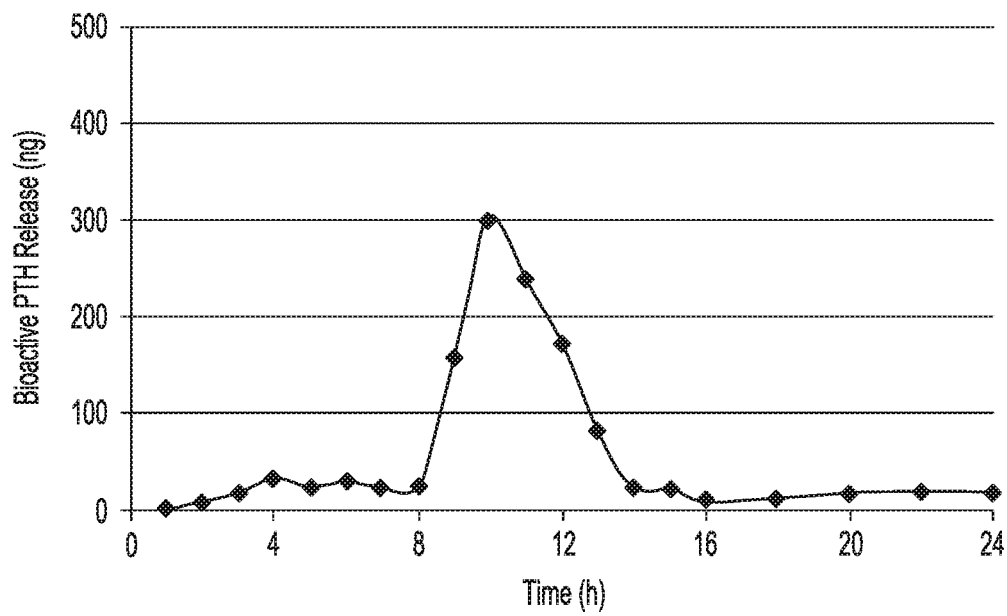
Figure 30C:
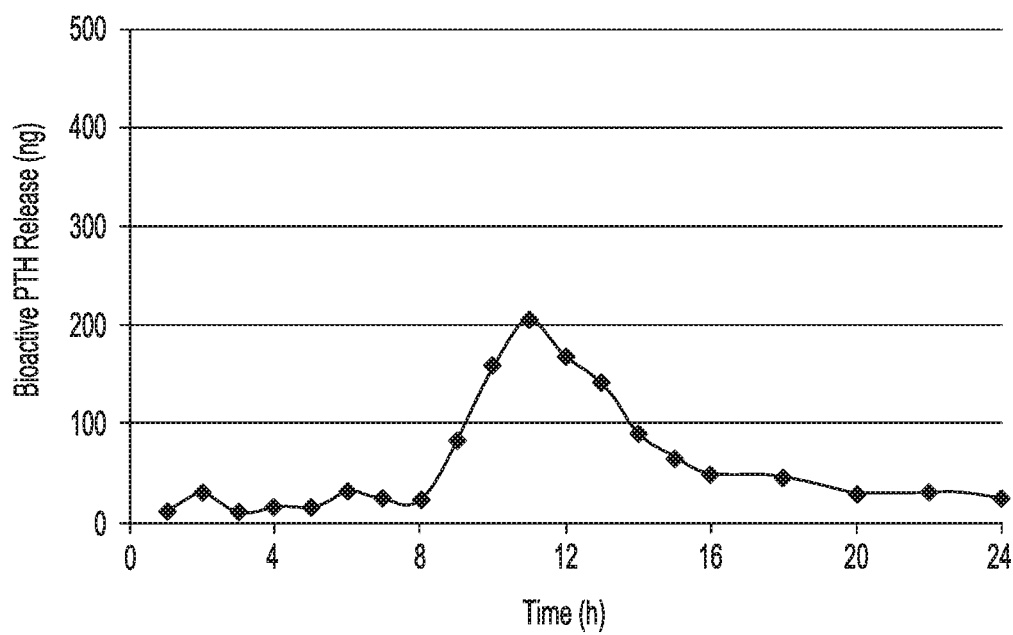
Figure 30D:
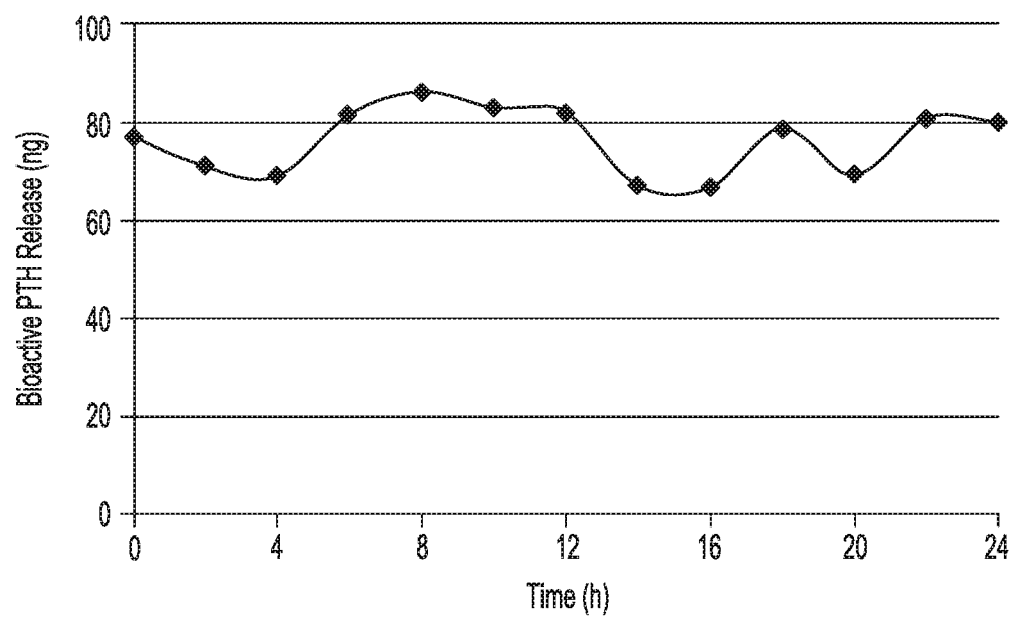
FIGS. 30D through 30F are graphs graph depicting the in vitro bioactive PTH release curves (ng versus hours) from the continuous delivery device of Example 2 on day 1, day 10, and day 20, respectively.
Figure 30E:
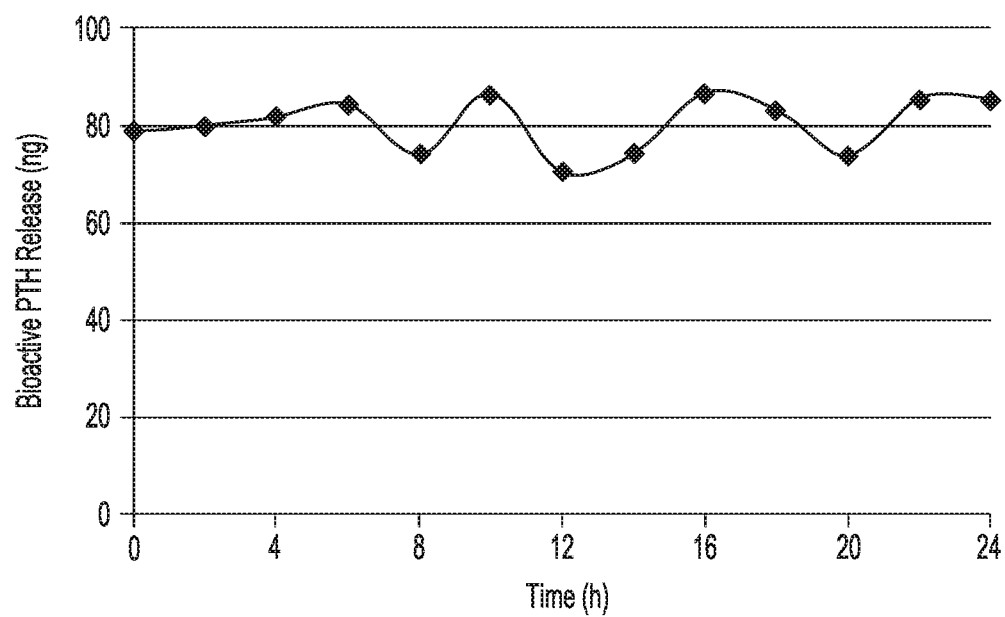
Figure 30F:
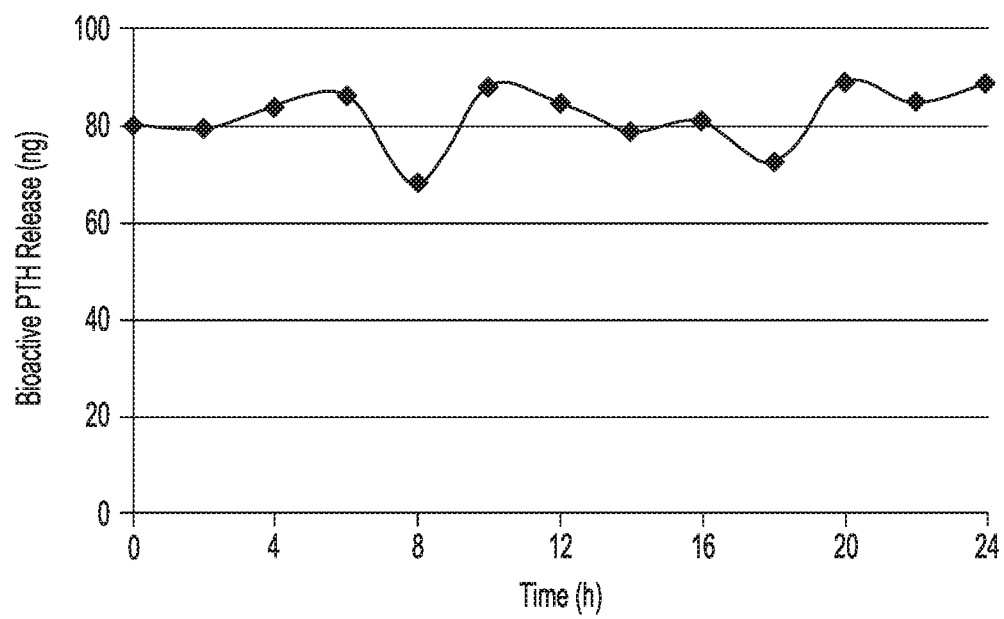

In addition, the released PTH from both types of devices was collected every hour on days 1, 10 and 20. The bioactivity of the released PTH was determined using the adenylyl cyclase stimulation and cAMP binding assay. The released bioactive PTH data showed that pulsatile PTH release devolved from a sharp peak (day 1) to a relatively broader peak (day 20) over time (FIGS. 30A (day 1 sample), 30B (day 10 sample), and 30C (day 20 sample)). This may have been due to the increased diffusion distance of PTH through the residual PA layers. However, the pulsatile release feature was maintained over the 21 days. The bioactive PTH was released at a steady rate from the continuous device (FIGS. 30D (day 1 sample), 30E (day 10 sample), and 30F (day 20 sample)), which was consistent with the linear release behavior shown from the ELISA data (FIG. 29).

In Vivo Testing

To determine the optimal PTH release mode to ensure desired PTH anabolic action in bone regeneration, the pulsatile PTH delivery device and the continuous PTH delivery device were compared in identical experimental set ups to access the outcomes of bone regeneration in a critical size (2.3 mm in diameter) round defect created in the mouse skull. The BSA loaded pulsatile devices were used as vehicle controls. All animal procedures were performed following a protocol approved by the University of Michigan Institutional Animal Care and Use Committee. C57BL/6 mice were randomly divided into four groups. Animals were anaesthetized with isoflurane (2%) inhalation. The 2.3 mm diameter craniotomy defect centered on the parietal calvarial bone was created using a trephine. A blank nanofibrous scaffold was placed to fill in the defect and a delivery device (pulsatile PTH, continuous PTH, or BSA control device) was placed adjacent to the scaffold with the opening side facing the scaffold (see FIG. 24).

In a positive control group (i.e., a PTH injection group), the mice did not receive any PTH delivery devices. Rather, PTH was subcutaneously injected for 3 weeks (21 days) using a standard systemic administration dose (40 μg/kg/d). Both the pulsatile devices and continuous devices were loaded with the same amount of PTH as the total standard injection amount.

All mice were euthanized 8 weeks after implantation. The skull and tibiae were harvested.

Figure 31:
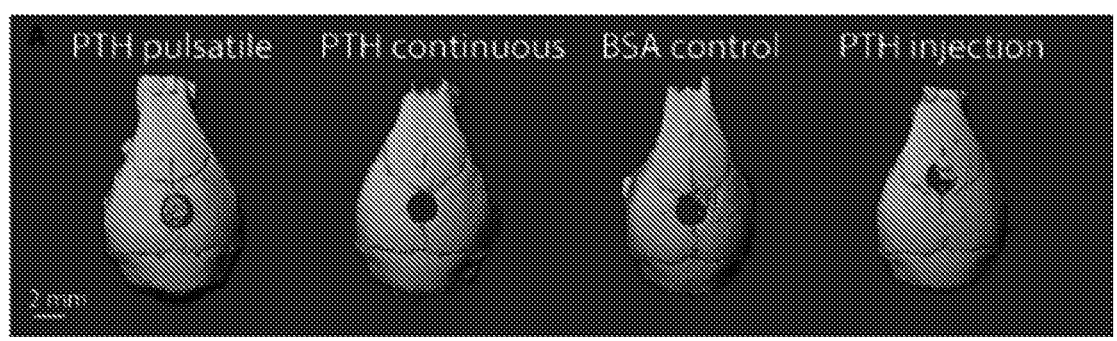
Figure 32A:
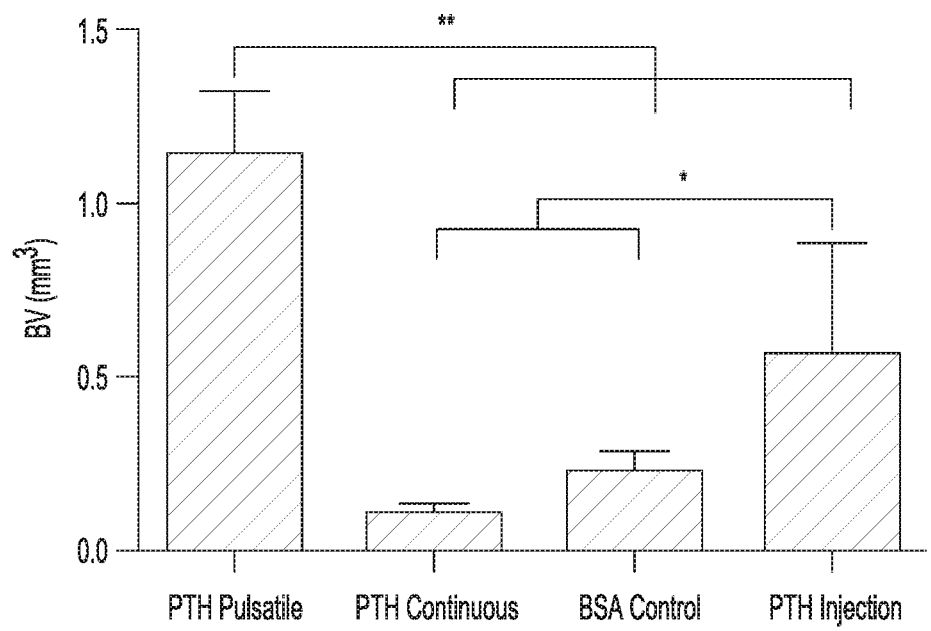
FIGS. 32A and 32B are graphs respectively depicting the new bone volumes (BV, $mm^3$) and new bone mineral density (BMD, mg hydroxyapatite (HA)/cubic centimeter (CCM)) of the mouse calvarials treated with the pulsatile PTH delivery device of Example 2, the continuous PTH delivery device of Example 2, the pulsatile BSA control device of Example 2, and the PTH injection (n=6-9 per group, $P^*<0.05$, $^{**}P<0.005$)
Figure 32B:
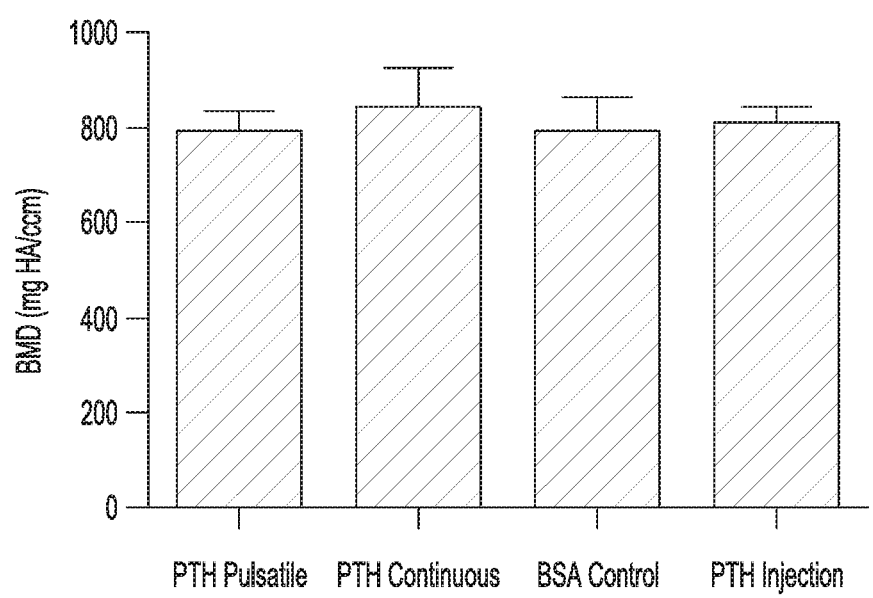

For the calvarial bone analysis, the skulls were scanned with a fixed global threshold of 20%. 3D reconstruction of the skull and quantitative analyses were performed. A 2.3 mm-round region of interest centered on the defect was determined and the bone volume (mm$^3$) (BV) and bone mineral density (BMD) in the area were measured using manufacturer's software (Scanco μCT 100). The μCT reconstruction of the skulls is shown in FIG. 31. These images showed that local pulsatile PTH release resulted in the best regeneration outcome among all groups, whereas continuous PTH release resulted in less bone compared to the BSA control group. As illustrated in FIGS. 32A and 32B, the new bone volume (FIG. 32A) was significantly more with the pulsatile PTH release, while the new bone mineral density (FIG. 32B) was comparable among the groups.

The calvarial samples were fixed with 4% formalin, decalcified with 10% EDTA for 2 weeks and subsequently embedded in paraffin. Hematoxylin & eosin (H&E) staining of the coronal sections (5 μm thick) were performed by the histology core at the University of Michigan School of Dentistry. Tartrate-resistant acid phosphatase (TRAP) staining was performed using the Leukocyte Acid Phosphatase Assay (Sigma) following the manufacturer's protocol. Bone static histomorphometric analyses for bone area and osteoclast number were performed using a computer-assisted histomorphometricm analyzing system (Image-Pro Plus version 4.0; Media Cybernetics, Inc., Silver Spring, Md.).

Figure 33B:
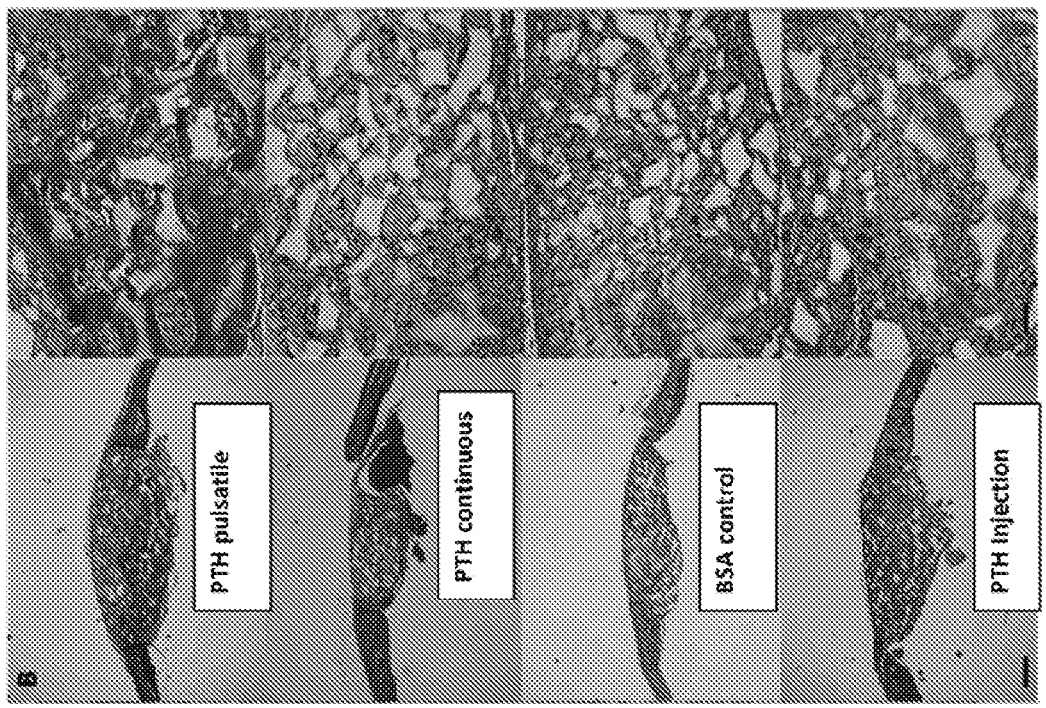
FIGS. 33A through 33C depict the histological characterization of the mouse calvarial bone defect repair 8 weeks after implantation, where 33A is a black and white image of H&E staining, 33B is a black and white image of Trichrome staining, and 33C is a black and white image of TRAP staining (scale bar: 0.5 mm in the left columns and 0.2 mm in the right columns)
Figure 33A:
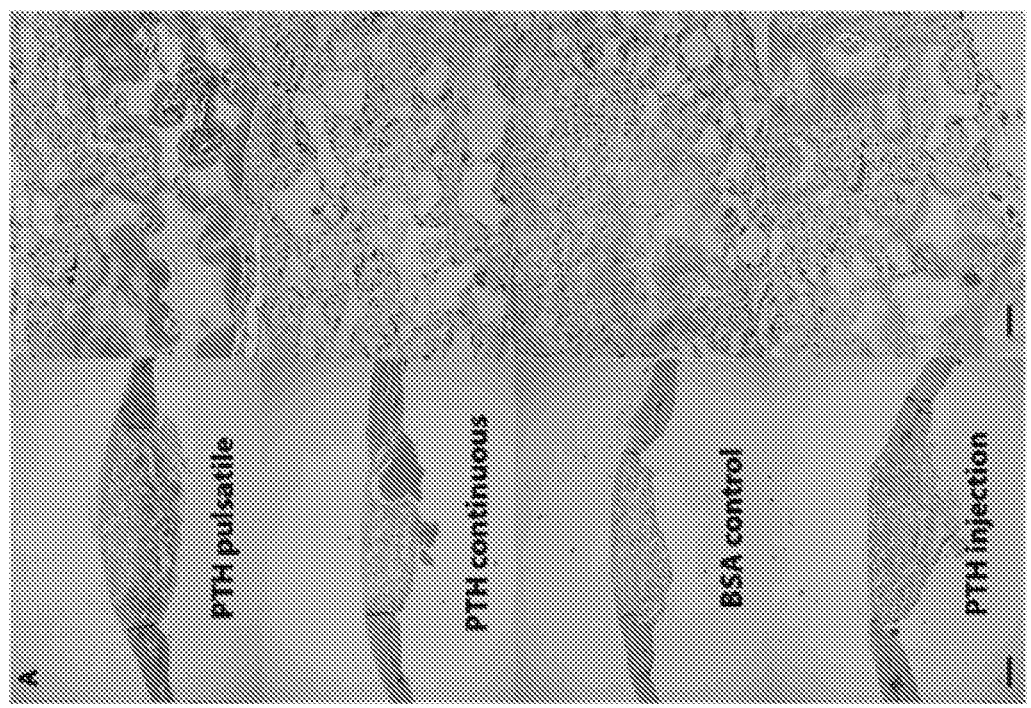

H&E (FIG. 33A, shown in black and white) and Trichrome staining (FIG. 33B, shown in black and white) showed that in the pulsatile PTH group, collagen-rich bone tissue (stained pink in H&E staining and dark blue in Trichrome staining) was formed throughout the scaffold, whereas only fibrous tissue was present in the continuous PTH group.

Figure 34A:
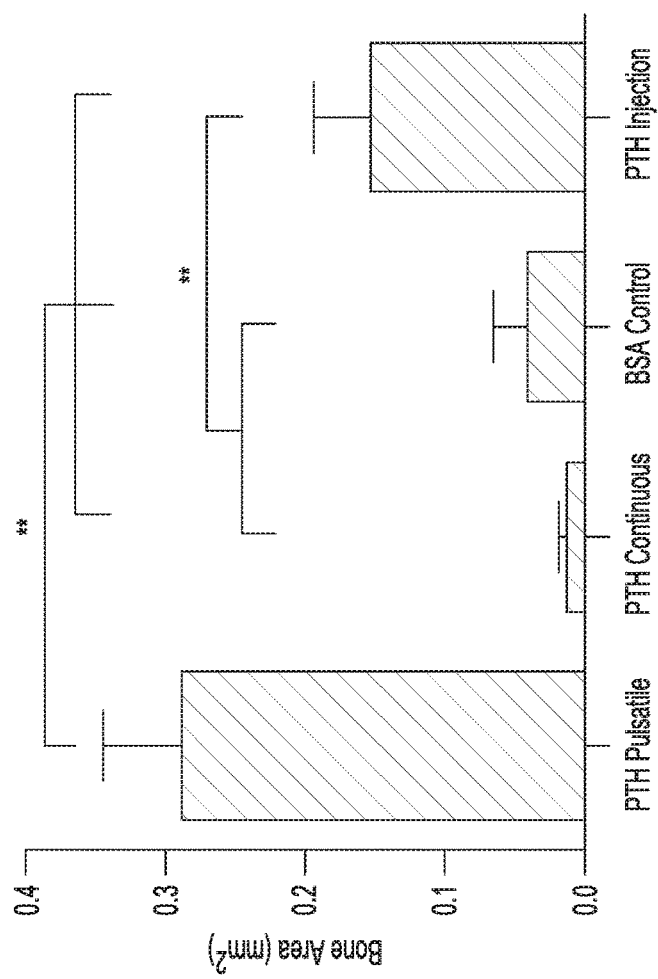
FIGS. 34A through 34C are graphs depicting the quantitative analysis of the mouse calvarial bone defect repair 8 weeks after implantation using histomorphometry, where 34A depicts the newly formed bone areas ($mm^2$), 34B depicts the TRAP positive osteoclasts numbers per area (OC #/$mm^2$), and 34C depicts the distribution of the osteoclasts in the bone area and scaffold area (n=6~9 per group, $^*P<0.05$, $^{**}P<0.005$)

Areas and volumes of newly formed bone were quantitatively analyzed using μCT and histomorphometry, revealing that the PTH injection significantly promoted bone growth in the nanofibrous scaffold compared to the control BSA group. Further, local pulsatile PTH release significantly increased bone volume and connected bone tissue regeneration even compared to systemic PTH injection (see FIGS. 32B and 34A).

Figure 33C:
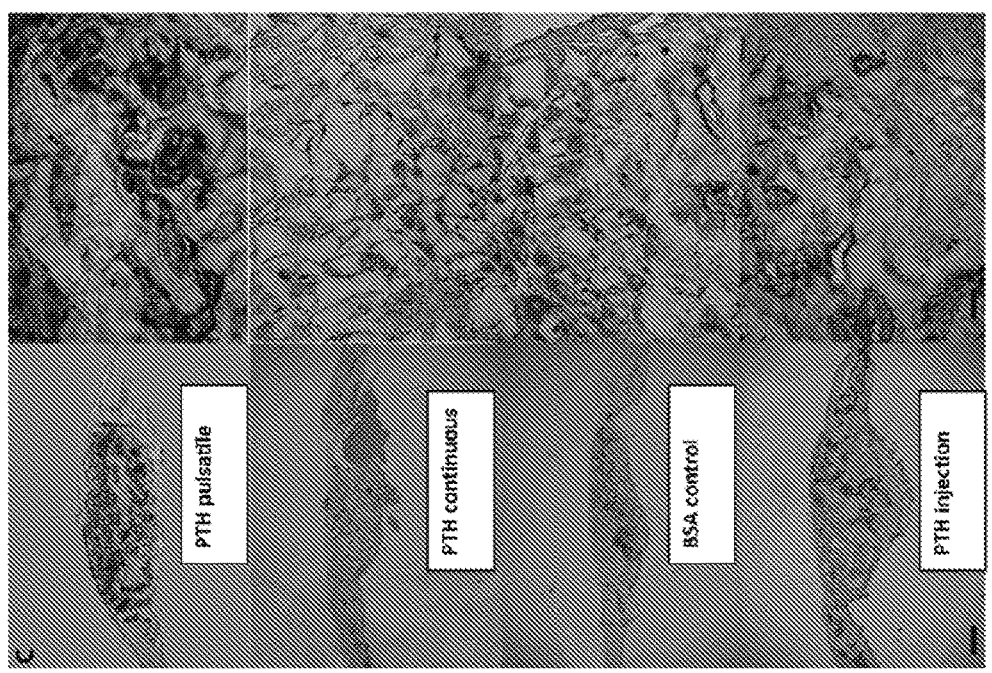
Figure 34B:
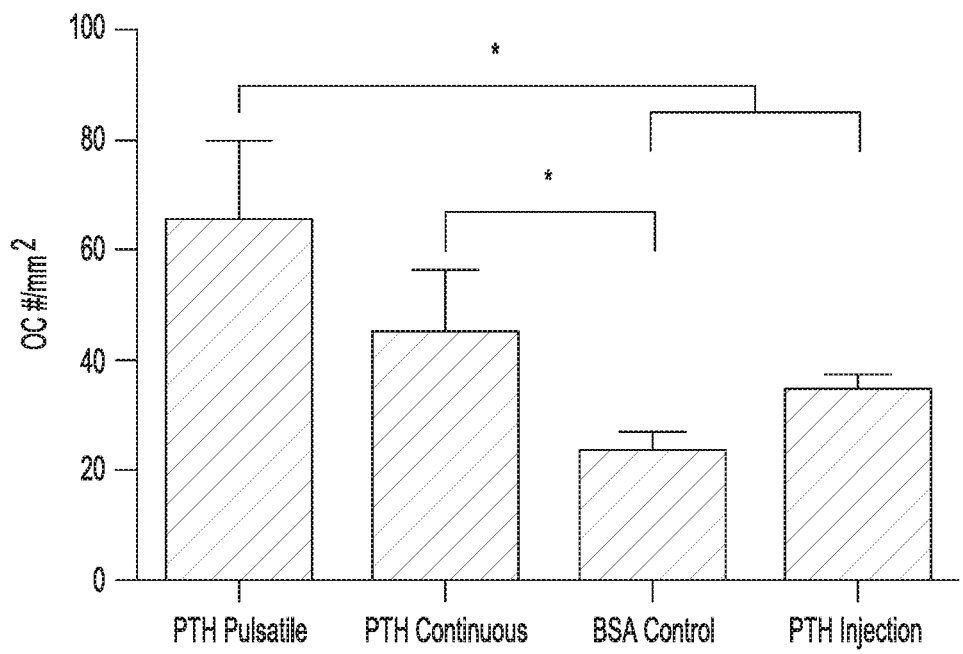
Figure 34C:
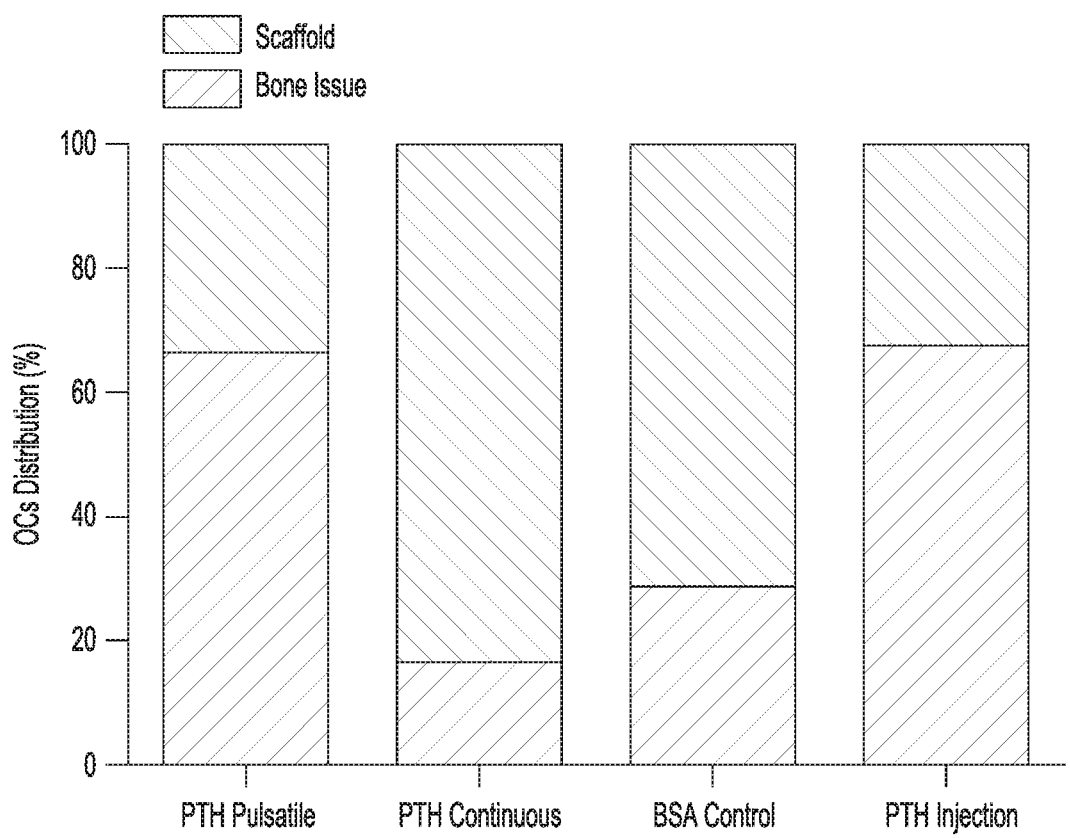

TRAP staining (FIG. 33C, shown in black and white) and the resultant osteoclast analysis (FIGS. 34B and 34C) showed that both pulsatile and continuous PTH release devices increased the number of osteoclasts compared to BSA controls. Over 60% of the osteoclasts were aligned along the new bone tissue in the pulsatile PTH group, while most of the TRAP positive cells (over 85%) in the continuous PTH group were found distributed throughout the fibrous tissue inside the scaffold. The osteoclast distribution in the local pulsatile and the systemic injection groups were similar, but local delivery recruited significantly more osteoclasts.

Mouse tibiae from the different groups were examined using μCT to assess the potential systemic side effects of the local PTH releases. For the tibiae μCT analyses, tibiae were scanned over the entire length. A fixed global threshold of 18% (180 on a grayscale of 0-1000) was used to segment trabecular bone from non-bone areas. A region of 0.75 mm right below the growth plate was analyzed to quantify the trabecular bone volume.

Figure 35:
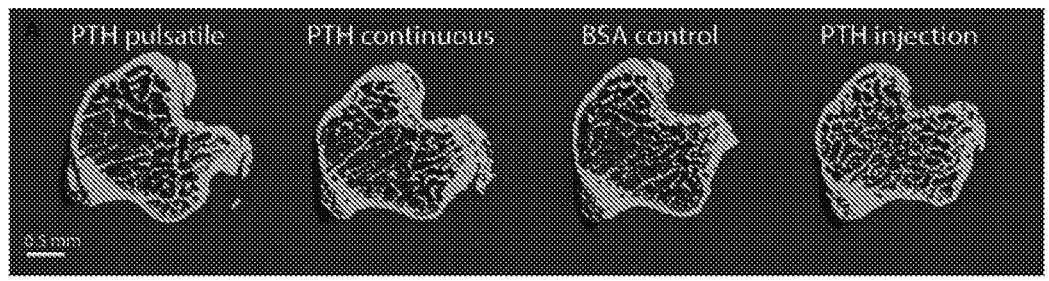
FIG. 35 illustrates, in black and white, the representative μCT reconstruction of the mouse tibia treated with the pulsatile PTH delivery device of Example 2, the continuous PTH delivery device of Example 2, the pulsatile BSA control device of Example 2, and the PTH injection.
Figure 36A:
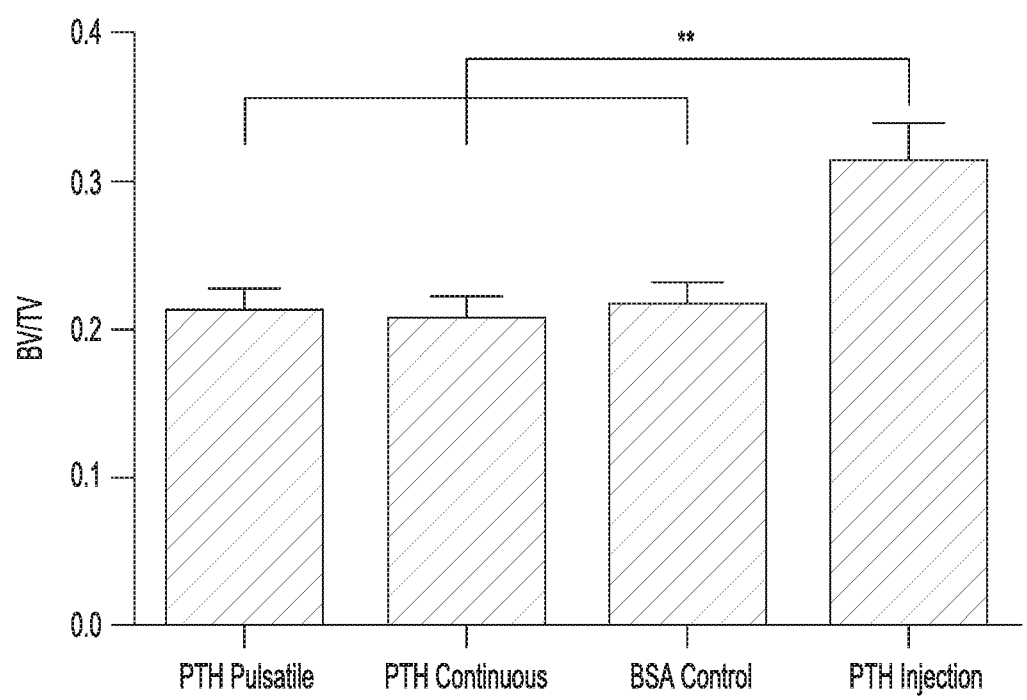
FIGS. 36A through 36C are graphs respectively depicting the trabecular bone volume (BV/TV), Serum P1NP level (pg/ml), and TRAP5b level (U/L) for the mouse tibia treated with the pulsatile PTH delivery device of Example 2, the continuous PTH delivery device of Example 2, pulsatile BSA control device of Example 2, and the PTH injection (n=6-9 per group, $P^*<0.05$, $^{**}P<0.005$).

As expected, 3 weeks of PTH injection significantly increased trabecular bone volumes. PTH released from the local device, both pulsatile and continuous, however, did not affect the trabecular bone, such that the volume of the trabecular bone remained unchanged compared to the BSA control group (see FIGS. 35 and 36A).

Figure 36B:
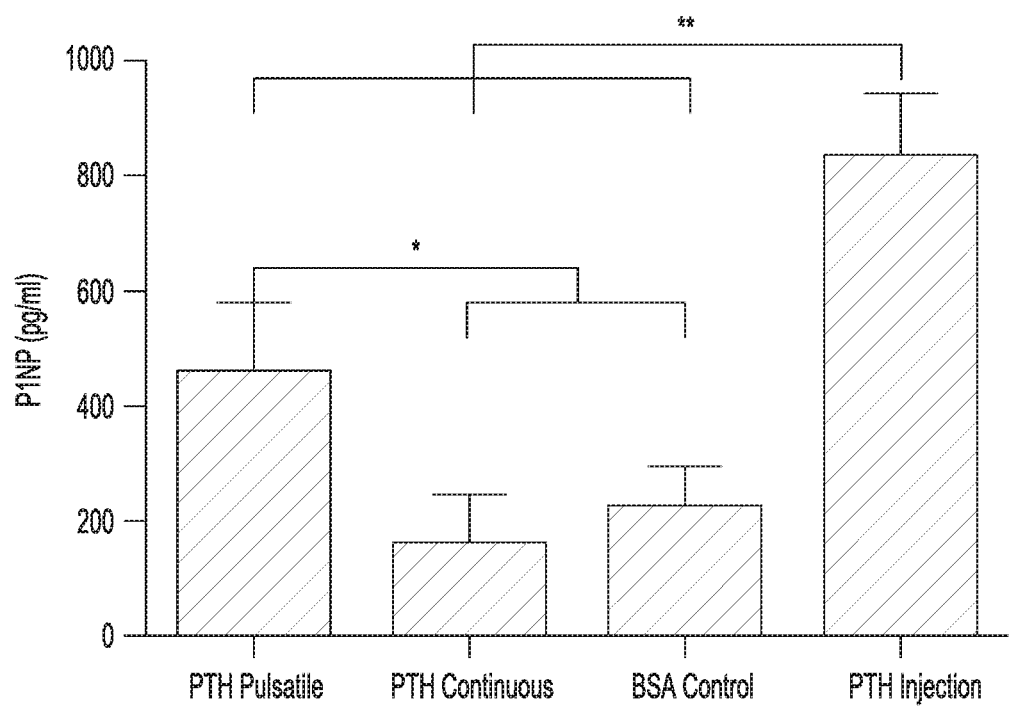
Figure 36C:
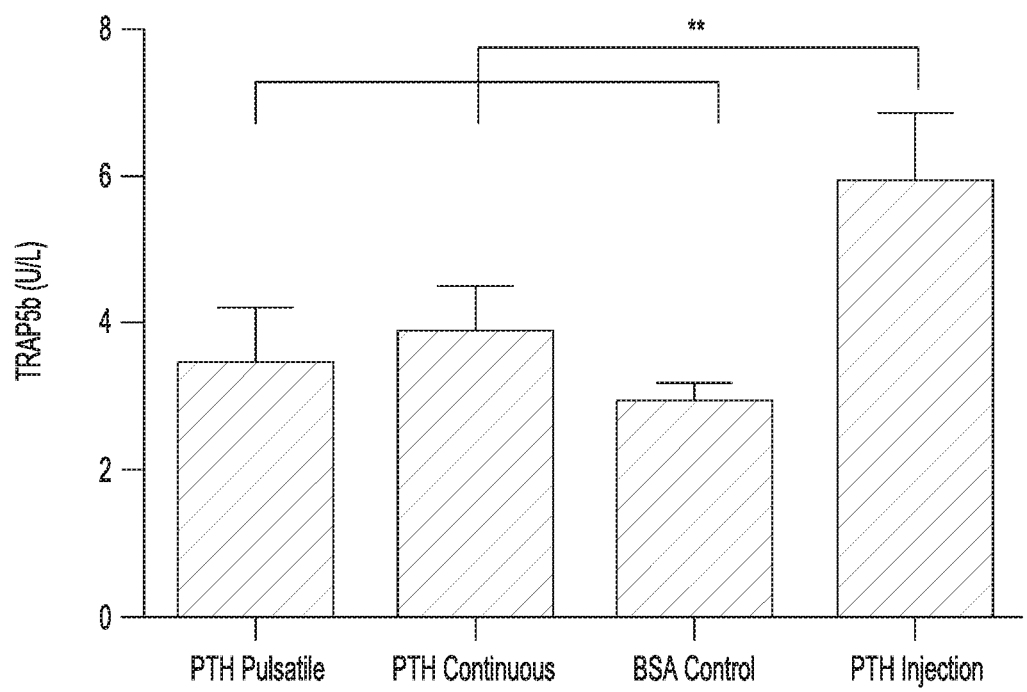

Three weeks after implantation, the mice were anaesthetized with inhalation of isoflurane (2%) and blood was collected by tail blood draw. After centrifuge for 10 minutes at 13000 rpm, serum was separated and kept frozen until biochemical assays were performed. Serum procollagen I N-terminal propeptide (P1NP) (MyBioSource, Inc) and TRAP5b (Novatein Biosciences, Mass.) ELISA immunoassays were performed following the manufacturer's protocols. The ELISA analyses were employed to evaluate the levels of bone biomarkers. Serum P1NP (bone formation marker) and TRAP5b (bone resorption marker) suggested that the intermittent systemic injection of PTH increased systemic bone turnover, as the levels of P1NP and TRAP5b in the blood were significantly elevated compared to the local delivery groups (FIGS. 36B and 36C).

Conclusion

In this Example, bone defect repair was achieved using local pulsatile PTH delivery. The success of repurposing PTH from osteoporosis to bone regeneration was achieved by developing a long-term pulsatile PTH delivery device to accurately deliver PTH to the defect sites to induce local anabolic effects. PTH treatments often rely on systemic administration that, in this Example, was shown to be less effective in enhancing local defect repair and to have unintended systemic side effects. Local treatment, on the contrary, has advantages such as maintaining relatively higher local bioactive agent levels, need for reduced dose concentration or number of dosages, and circumventing possible adverse side effects resulting from systemic administration.

The highly porous nanofibrous scaffold was used to evaluate the two engineered PTH release modes for regeneration purpose. The PLLA scaffolds with nanofibrous surface features were previously shown to selectively enhance the adsorption of cell-adhesion proteins including fibronectin and vitronectin, increasing osteoblast adhesion. Additionally, such nanofibrous scaffolds enhance the osteoblastic differentiation of a variety of stem cells, including BMSCs, which are integral for bone defect healing. In this Example, the histological cross-section of the control group (scaffold with BSA delivery) also supported the conclusion that the NF structure alone could induce certain level of bone formation in vivo (FIGS. 31 and 32A).

Furthermore, with different PTH release kinetics incorporated, distinct osteogenic outcomes in the nanofibrous scaffolds were observed. Local pulsatile PTH delivery significantly improved the defect repair, generating connected and robust new bone tissue throughout the scaffold, whereas local continuous delivery resulted in less bone in the NF scaffold versus the BSA control group.

From the TRAP staining data (FIG. 33C, shown in black and white), it was observed that both PTH releases, pulsatile and continuous, were able to increase osteoclast numbers. Pulsatile PTH release induced stronger bone remodeling with enhanced numbers of the osteoclasts aligned along the formed bone tissue, while continuous PTH release resulted in reduced bone, with increased osteoclasts, not lining the bone, but throughout the fibrous tissue inside the scaffold. The results indicate that the local pulsatile PTH release was able to induce beneficial catabolic actions by stimulating osteoclasts to realize the needed bone remodeling activity in this specific bone-regeneration scenario.

In comparing the local pulsatile PTH release device with the standard systemic PTH injection treatment, it was found that local release was advantageous over the systemic injection in improving the defect repair. This local strategy may have benefitted from the more localized higher bioactive PTH level and the longer action time in the local defect sites. Given the 8 minute half-life of PTH, only a part of the total bioactive PTH could reach the defect sites considering the bioactivity loss during circulation time when PTH is given systemically. On the contrary, the local delivery strategy is more likely to maintain bioactive PTH level within an effective range for a period of time.

In addition to enhancing local defect repair, local PTH releases led to little undesired systemic effects, whereas PTH systemic injection resulted in clear systemic effects as expected. The μCT and serum data showed that PTH injection significantly increased tibiae trabecular bone volume and serum biomarkers, while PTH local release did not affect tibiae trabecular bone and exerted only minor, if any, effects on serum bone biomarkers. These results indicate that PTH release from the device was likely to be delivered and act more locally.

The polymeric materials used in this system, PLLA, PA, PCL and alginate, are biodegradable and FDA-approved materials for certain medical applications. The devices will degrade/erode over time and the degradation by-products elicit minimum immune reaction in vivo, which is particularly advantageous for the defect repair application. In addition, this approach needs only a one-time administration (implantation) instead of daily injection for 3 weeks and there is no need for retrieval of the empty devices after the drug release is complete. Therefore, the implantable devices are more patient-friendly and are promising for clinical translation.

Overall, the example delivery devices 10, 10' disclosed herein may be utilized for bone defect generation without addition of external cells, the burden of daily PTH injections, or the need for device removal surgery. It is believed that the devices 10, 10' could also be readily employed to deliver other therapeutics or their combinations in a tailored manner to maximize their therapeutic effects.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range. For example, a range from about 8 hours to about 24 hours should be interpreted to include not only the explicitly recited limits of about 8 hours to about 24 hours, but also to include individual values, such as 9 hours, 12.5 hours, etc., and sub-ranges, such as from about 10 hours to about 20.2 hours, from about 14 hours to about 18 hours, etc. Furthermore, when "about" is utilized to describe a value, this is meant to encompass minor variations (up to +/−10%) from the stated value.

In describing and claiming the examples disclosed herein, the singular forms "a", "an", and "the" include plural referents unless the context clearly dictates otherwise.

While several examples have been described in detail, it is to be understood that the disclosed examples may be modified. Therefore, the foregoing description is to be considered non-limiting.

What is claimed is:

1. A pulsatile delivery device, comprising:
a stack of at least two bi-layer structures, each bi-layer structure including:
a delivery layer including a film forming material and a predetermined substance dispersed throughout the film forming material, the delivery layer having a negatively charged surface; and
a positively charged surface of a polymeric layer electrostatically attached to the negatively charged surface of the delivery layer, the polymeric layer being selected from the group consisting of a two-component copolymer of a sebacic acid anhydride precursor and a 1,3-bis(carboxyphenoxy) propane anhydride precursor and a three-component copolymer of a sebacic acid anhydride precursor, a 1,3-bis(carboxyphenoxy) propane anhydride precursor, and a poly(ethylene glycol) anhydride precursor; and
a sealant partially surrounding the stack so that one of the polymeric layers of the stack is exposed.

2. The pulsatile delivery device as defined in claim 1 wherein the electrostatic attachment substantially eliminates air gaps between the layers of each bi-layer structure.

3. The pulsatile delivery device as defined in claim 1, wherein the film forming material of the delivery layer is selected from the group consisting of alginate, collagen, gelatin, hyaluronic acid, starch, glycogen, cellulose, caragena, dextran, chitin, chitosan, pectin, heparin, heparan sulfate, copolymers thereof, and combinations thereof.

4. A pulsatile delivery device, comprising:
- a stack of at least two bi-layer structures, each bi-layer structure including:
  - a delivery layer including a film forming material and a predetermined substance dispersed throughout the film forming material; and
  - a polymeric layer electrostatically attached to the delivery layer; and
- a sealant partially surrounding the stack so that one of the polymeric layers of the stack is exposed;
- wherein prior to being electrostatically attached, the polymeric layer has an electrostatic voltage of about +157 mV ±67 mV and the delivery layer has an electrostatic voltage of about −80 mV ±30 mV.

5. The pulsatile delivery device as defined in claim 4, wherein the film forming material is alginate, the predetermined substance is parathyroid hormone, and the polymeric layer is polyanhydride.

6. A method for making the pulsatile delivery device of claim 4, the method comprising:
- generating positive charges on the polymeric layer such that the polymeric layer has an electrostatic voltage of about +157 mV ±67 mV;
- generating negative charges on the delivery layer such that the delivery layer has an electrostatic voltage of about −80 mV ±30 mV;
- placing the charged polymeric layer and delivery layer in contact to form a respective one of the at least two bi-layer structures;
- forming the stack with the at least two bi-layer structures so that the polymeric layers and the delivery layers are alternating throughout the stack; and
- sealing the stack with the sealant so that one of the polymeric layers of the stack is exposed.

7. The method as defined in claim 6 wherein the stack is positioned on an elastic sealant layer, and wherein the sealant is an elastic sealant material and sealing the stack includes coating the elastic sealant material on an outer edge of the stack.

8. The method as defined in claim 7 wherein coating the elastic sealant material includes casting a solution of the elastic sealant material on the outer edge of the stack to form a construct, and wherein the method further comprises:
- subjecting the construct to vacuum;
- repeating the casting and subjecting; and
- drying the construct.

9. The method as defined in claim 6 wherein:
- the generating of the positive charges on the polymeric layer is accomplished by rubbing a surface with a polytetrafluoroethylene film; and
- the generating of the negative charges on the delivery layer is accomplished by rubbing a surface with a glass slide.

10. The method as defined in claim 6 wherein the sealant is an elastic sealant material and sealing the stack includes coating the elastic sealant material on a cylindrical side of the stack.

11. The method as defined in claim 6 wherein the stack is formed with at least ten bi-layer structures.

12. The method as defined in claim 6 wherein the polymeric layer is polyanhydride, the predetermined substance is parathyroid hormone, and the film forming material is alginate.

* * * * *